US008632816B2

(12) United States Patent
Sojka et al.

(10) Patent No.: US 8,632,816 B2
(45) Date of Patent: *Jan. 21, 2014

(54) COMPOSITIONS COMPRISING SOLID PARTICLES ENTRAPPED IN COLLAPSED POLYMERIC MICROSPHERES, AND METHODS OF MAKING THE SAME

(75) Inventors: Milan F. Sojka, Coram, NY (US); Phillip Cummins, Livingston, NJ (US); Christina G. Fthenakis, Dix Hills, NY (US); Jean Harry Xavier, Holbrook, NY (US)

(73) Assignee: ELC Management, LLC, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/426,951

(22) Filed: Mar. 22, 2012

(65) Prior Publication Data

US 2013/0071453 A1 Mar. 21, 2013

Related U.S. Application Data

(63) Continuation-in-part of application No. 12/138,742, filed on Jun. 13, 2008, now abandoned.

(60) Provisional application No. 61/014,235, filed on Dec. 17, 2007.

(51) Int. Cl.
*A61Q 17/04* (2006.01)
*A61Q 19/00* (2006.01)
*A61K 8/04* (2006.01)
*A61K 8/02* (2006.01)
*A61K 8/81* (2006.01)

(52) U.S. Cl.
CPC ............... *A61Q 17/04* (2013.01); *A61Q 19/00* (2013.01); *A61K 8/042* (2013.01); *A61K 8/0287* (2013.01); *A61K 8/8152* (2013.01); *A61K 8/8123* (2013.01)
USPC ............... 424/497; 424/59; 424/60; 424/401

(58) Field of Classification Search
None
See application file for complete search history.

(56) References Cited

U.S. PATENT DOCUMENTS

| | | | |
|---|---|---|---|
| 1,964,682 A | 6/1934 | Ayers | |
| 3,615,972 A * | 10/1971 | Morehouse et al. | 156/79 |
| 3,864,181 A | 2/1975 | Wolinski et al. | |
| 4,006,223 A | 2/1977 | Chitulescu et al. | |
| 4,044,176 A | 8/1977 | Wolinski et al. | |
| 4,366,827 A | 1/1983 | Madrange et al. | |
| 4,397,799 A | 8/1983 | Edgren et al. | |
| 4,513,106 A | 4/1985 | Edgren et al. | |
| 4,671,955 A | 6/1987 | Palinczar | |
| 4,722,943 A | 2/1988 | Melber et al. | |
| 4,962,170 A | 10/1990 | Chromecek et al. | |
| 5,219,561 A | 6/1993 | Gagnebien et al. | |
| 5,223,250 A | 6/1993 | Mitchell et al. | |
| 5,314,683 A | 5/1994 | Schlossman | |
| 5,393,809 A | 2/1995 | Gueret | |
| 5,451,610 A | 9/1995 | Krzysik | |
| 5,452,584 A | 9/1995 | Diggs | |
| 5,593,680 A | 1/1997 | Bara et al. | |
| 5,635,109 A | 6/1997 | Otsuka | |
| 5,733,531 A | 3/1998 | Mitchnick et al. | |
| 5,733,572 A | 3/1998 | Unger et al. | |
| 5,747,010 A | 5/1998 | Geesin et al. | |
| 5,755,998 A | 5/1998 | Yamazaki et al. | |
| 5,817,299 A | 10/1998 | Manirazman | |
| 5,851,538 A | 12/1998 | Froix et al. | |
| 5,955,091 A * | 9/1999 | Hansenne | 424/401 |
| 6,096,331 A | 8/2000 | Desai et al. | |
| 6,146,649 A * | 11/2000 | Hansenne | 424/401 |
| 6,254,877 B1 | 7/2001 | DeLaPoterie et al. | |
| 6,313,181 B1 | 11/2001 | Cohen | |
| 6,592,882 B2 | 7/2003 | George et al. | |
| 6,753,002 B2 | 6/2004 | George et al. | |
| 6,814,959 B1 | 11/2004 | Müller et al. | |
| 8,383,160 B2 * | 2/2013 | Sojka et al. | 424/497 |
| 2001/0007710 A1 | 7/2001 | Liu et al. | |
| 2003/0108492 A1 | 6/2003 | Chaudhuri | |
| 2003/0124071 A1 | 7/2003 | Candau et al. | |
| 2003/0215394 A1 | 11/2003 | Short et al. | |
| 2004/0141933 A1 | 7/2004 | Luo et al. | |

(Continued)

FOREIGN PATENT DOCUMENTS

| | | |
|---|---|---|
| CA | 2330863 | 11/1999 |
| DE | 2521003 | 8/1976 |

(Continued)

OTHER PUBLICATIONS

Ahamad, M.; Flexible Vinyl Resiliency Property Enhancement With Hollow Thermoplastic Microspheres; Journal of Vinyl & Additive Tech; vol. 7; No. 3; pp. 156-161; Sep. 2001.
An Introduction to Expancel Microspheres; An Introduction; Akzo Nobel; www.Expancel.com; No Publication Date Available; 2004.
PCT International Search Report; International Application No. PCT/US2006/037207; Completion Date: Jan. 24, 2007; Date of Mailing: Jan. 24, 2007.
PCT Written Opinion of the International Searching Authority; International Application No. PCT/US2006/037207; Completion Date: Jan. 24, 2007; Date of Mailing: Jan. 24, 2007.
Takatsugu Yoshioka; New ingredients and application for ultraviolet-ray protection; Fragrance Journal, Japan; vol. 27; No. 5; pp. 62-70; May 1999, (Eng. Trans.).

(Continued)

*Primary Examiner* — Frederick Krass
*Assistant Examiner* — Isaac Shomer
(74) *Attorney, Agent, or Firm* — Cynthia R. Miller

(57) ABSTRACT

The present invention relates to topical compositions containing solid particles that are stabilized via entrapment by microspheres and methods for making the same. Each of the microspheres contains a collapsed polymeric shell that has entrapped therein one or more solid particles. The solid particles are preferably formed of zinc oxide or titanium dioxide or both, which can readily be used either alone or in combination with other sunscreen agents to form sunscreen compositions of broader UV protection spectrum and enhanced photostability.

37 Claims, 6 Drawing Sheets

(56) References Cited

U.S. PATENT DOCUMENTS

| | | |
|---|---|---|
| 2004/0161395 A1 | 8/2004 | Patil et al. |
| 2004/0228886 A1 | 11/2004 | Ding et al. |
| 2005/0112154 A1 | 5/2005 | Giroud et al. |
| 2005/0129759 A1* | 6/2005 | Sojka ............................ 424/469 |
| 2005/0208005 A1 | 9/2005 | Giroud |
| 2005/0244349 A1 | 11/2005 | Chaudhuri et al. |
| 2005/0249682 A1 | 11/2005 | Buseman-Williams et al. |
| 2006/0153889 A1 | 7/2006 | Friel et al. |
| 2007/0071978 A1* | 3/2007 | Sojka et al. ................ 428/402.2 |
| 2009/0155371 A1 | 6/2009 | Sojka et al. |

FOREIGN PATENT DOCUMENTS

| | | |
|---|---|---|
| EP | 0056219 | 7/1982 |
| EP | 0112807 | 7/1984 |
| EP | 0585239 | 9/1998 |
| FR | 2 700 952 | 8/1994 |
| GB | 2237574 | 5/1991 |
| JP | 60-184004 | 9/1985 |
| JP | 3025436 | 2/1991 |
| JP | 3-267140 | 11/1991 |
| JP | 10-338612 | 12/1998 |
| JP | 11-100311 | 4/1999 |
| JP | 2000-072645 | 3/2000 |
| JP | 2005-154649 | 6/2005 |
| JP | 2006-290767 | 10/2006 |
| JP | 2006-307005 | 11/2006 |
| JP | 2007-002000 | 1/2007 |
| JP | 2007-002001 | 1/2007 |
| JP | 2007-160287 | 6/2007 |
| KR | 2002-0079131 | 10/2002 |
| WO | WO00/41528 | 7/2000 |
| WO | WO2007/038404 | 5/2007 |

OTHER PUBLICATIONS

Brown, et al.; Bicyclic monoterpene diols stimulate release of nitric oxide from skin cells, increase microcirculation, and elevate skin temperature; Nitric Oxide Biology and Chemistry; Nitric Oxide 15; pp. 70-76; Feb. 2006.

PCT International Search Report; International Application No. PCT/US2008/083607; Completion Date: Jun. 16, 2009; Date of Mailing: Jun. 16, 2009.

PCT Written Opinion of the International Searching Authority; International Application No. PCT/US2008/083607; Completion Date: Jun. 16, 2009; Mailing Date: Jun. 16, 2009.

Optisol™; Advanced UV Protection . . . ; Company Phamphlet; Croda Chemicals Europe Ltd.; 2006.

Creations Couleurs; Eospoly®; http://www.creationscouleurs.com/en/products/eospoly.html; 2004.

PCT International Search Report; International Application No. PCT/US2009/052683; Completion Date: Feb. 22, 2010; Date of Mailing: Feb. 24, 2010.

PCT Written Opinion of the International Searching Authority; International Application No. PCT/US2009/052683; Completion Date: Feb. 22, 2010; Date of Mailing: Feb. 24, 2010.

Maier, Harald, et al.; Change of Ultraviolet Absorbance of Sunscreens by Exposure to Solar-Simulated Radiation; The Journal of Investigative Dermatology; vol. 117, No. 2; pp. 256-262; 2001.

Lee, Wilson A., et al.; Multicomponent polymer coating to block photocatalytic activity of $TiO_2$ nanoparticles; Chemical Communications 45; pp. 4815-4817; 2007.

University of North Carolina Eshelman School of Pharmacy; Factors Influencing the Solubility of Drugs; http://pharmlabs.unc.edu/labs/solubility/structure.htm; Accessed Sep. 6, 2011. (3 pp.).

Supplementary European Search Report; EP08863316.9; Completion Date: Sep. 28, 2011; Date of Mailing: Oct. 11, 2011.

Azko Nobel. "Expancel® Microspheres." Apr. 2001, 2 printed pages. ®.

PCT International Search Report; International Application No. PCT/US2011/020655; Completion Date: Sep. 21, 2011; Date of Mailing: Sep. 21, 2011.

PCT Written Opinion of the International Searching Authority; International Application No. PCT/US2011/020655; Completion Date: Sep. 21, 2011; Date of Mailing: Sep. 21, 2011.

* cited by examiner

COMPOSITIONS COMPRISING SOLID PARTICLES ENTRAPPED IN COLLAPSED POLYMERIC MICROSPHERES, AND METHODS OF MAKING THE SAME

CROSS-REFERENCE TO RELATED APPLICATIONS

This application is a continuation-in-part of U.S. patent application Ser. No. 12/138,742, filed Jun. 13, 2008 now abandoned, which claims priority from U.S. Provisional Patent Application Ser. No. 61/014,235 filed Dec. 17, 2007.

FIELD OF THE INVENTION

The present invention relates to topical compositions comprising stabilized particulate components, as well as methods of making the same.

BACKGROUND OF THE INVENTION

Cosmetic or topical compositions typically comprise one or more particulate components, such as, for example, pigments or dyes, fillers, thickeners, sunscreen agents, and the like. Such particulate components are often insoluble in the respective solvent or carrier system and if so remain dispersed or suspended in the cosmetic or topical compositions.

However, whenever there are changes in the pH and temperature in the surrounding environment, the dispersed or suspended particles may agglomerate with one another and precipitate out of the composition. In physical sunscreen preparations, metal oxide particles, such as titanium dioxide ($TiO_2$) or zinc oxide (ZnO) particles are used for their ability to reflect an absorb UV radiation; however, their tendency to agglomerate favors an uneven distribution of the particles when the sunscreen is spread on the skin, resulting in a sun protection factor (SPF) which is much smaller than the expected SPF, with undesired consequences for the safety of the consumer.

Additionally, in such sunscreen compositions, metal oxide particles having a size appropriate to maintain them on the surface of the stratum corneum (i.e., with an apparent diameter larger than about 5 µm) scatter the incident solar radiation such that the topically applied sunscreen confers a white color to the skin. Topically applied micronized particles with an apparent diameter small than 100 nm scatter incident solar radiation and do not confer the undesired white color to the skin. However, concerns have been raised as to whether these particles remain the surface of the stratum corneum or penetrate further.

Irrespective of their size or of clustering, metal oxide particles which absorb solar UV radiation can transfer their energy to surrounding molecular oxygen, thus generating singlet oxygen. Singlet oxygen and other reactive oxygen species (ROS) generated by topically applied metal oxide particles under UV radiation can react with lipids and proteins in the stratum corneum and add to the direct and indirect damage generated by the residual radiation. Encapsulation or coating has been suggested as a way to circumvent, or at least decrease, the generation of ROS by $TiO_2$ particles. As an example, Published patent application Ser. No. 11/534,074, filed Sep. 21, 2006, the disclosure of which is herein incorporated in its entirety, describes hollow, thermoplastic microsphere-entrapped particulates, such as $TiO_2$. The microspheres, which may be of the Expancel type, are treated with a solvent which opens up pre-existing pores in their surfaces so that the particulates dissolved in the solvent may enter the surface pores, replacing a portion of the ambient gas, typically air. The particulates are thus adsorbed into surface pores of the microspheres. The solvents, which are used under ambient conditions and which are described as not strongly polar so as not to dissolve of break the particulates, include ethanol, hydrocarbons, such as hexane or heptanes, esters such as ethyl acetate, and volatile silicones such as cyclomethicone or low molecular weight dimethicone. Strongly polar solvents, such as acetone, DMF, DMS and strong mineral acids or bases are described as not useful. Once the adsorption is completed, the solvent may be evaporated off, resulting in a free-flowing powder. The microspheres, the interiors of which remain hollow, may be further treated by providing a polymeric coating on the surface which, depending upon the intended disposition of the particulates, can either delay or prevent release of the particulates directly onto the skin. There is no change in the size of the microspheres as a result of the treatment provided.

Further, the smaller the particle size, the larger the active surface area, and the more susceptible such particulate components are toward adverse interactions or interference with other ingredients or components in the cosmetic or topical compositions, which may destabilize the cosmetic or topical compositions or reduce the overall performance thereof.

There is therefore a continuing need for treating or modifying the particulate components of cosmetic or topical compositions in order to eliminate or mitigate the above-described drawbacks and improve the overall stability of the compositions without adversely affecting the chemical and physical properties of the particulate components.

There is also a need for improving the chemical and/or physical properties of the particulate components through surface treatment or modification.

SUMMARY OF THE INVENTION

In one aspect, the present invention relates to a method for modifying or treating solid particles, comprising:
(a) forming a gelled mixture by mixing either simultaneously or sequentially in any order
 (1) hollow microspheres each comprising a deformable polymeric shell having entrapped therein an expandable fluid,
 (2) an organic first solvent which is present in an amount sufficient to swell and implode the microspheres but not dissolve the polymeric shells of the hollow microspheres, and
 (3) solid particles,
wherein molecules of the first solvent enter between polymeric chains of the polymeric shell and disrupt intermolecular bonds between the chains, forming micro-channels in the swelled polymer shells which substantially simultaneously allow entry of the solid particles into the hollow microspheres and exit of a first portion of the expandable fluid therefrom, thereby collapsing the microspheres and entrapping the solid particles therein;
(b) introducing a second solvent which is miscible with the first solvent into the gelled mixture with sufficient agitation to quench the gelled mixture, thereby diluting the first solvent and permitting exit of a second portion of expandable fluid from the microspheres so as to form separated microspheres, each comprising a collapsed polymeric shell, having an average particle size in the range of from about 1 to about 50 microns, and having one or more of said solid particles entrapped therein; and
(c) removing the expandable fluid and solvents to result in a dry, free-flowing powder.

In a preferred embodiment of this aspect of the invention, the method further includes (d) coating the microspheres with a film-forming material to form a liquid-impermeable membrane thereon.

In a further aspect, the present invention relates to a microsphere comprising a collapsed polymeric shell having entrapped therein one or more solid particles, and the microsphere preferably, but not necessarily, being coated with a liquid-impermeable membrane.

In another aspect, the present invention relates to a topical composition comprising a dispersion of microspheres in a cosmetically or pharmaceutically acceptable carrier, wherein each of the microspheres comprises a collapsed polymeric shell having entrapped therein one or more solid particles, and the microspheres preferably, but not necessarily, being coated with a liquid-impermeable membrane.

In yet another aspect, the present invention relates to a topical sunscreen composition comprising a dispersion of microspheres in a cosmetically or pharmaceutically acceptable carrier, wherein each of the microspheres comprises a collapsed polymeric shell having entrapped therein one or more solid particles that comprise titanium dioxide, zinc oxide, or a combination thereof, and wherein each of the microspheres preferably, but not necessarily, comprises an organic sunscreen agent susceptible to oxidative decomposition or degradation, and wherein each of the microspheres is preferably, but not necessarily, coated with a film forming material forming a liquid-impermeable membrane thereon.

Other aspects and objectives of the present invention will become more apparent from the ensuing description, examples, and claims.

DETAILED DESCRIPTION OF THE INVENTION

Figure 1:
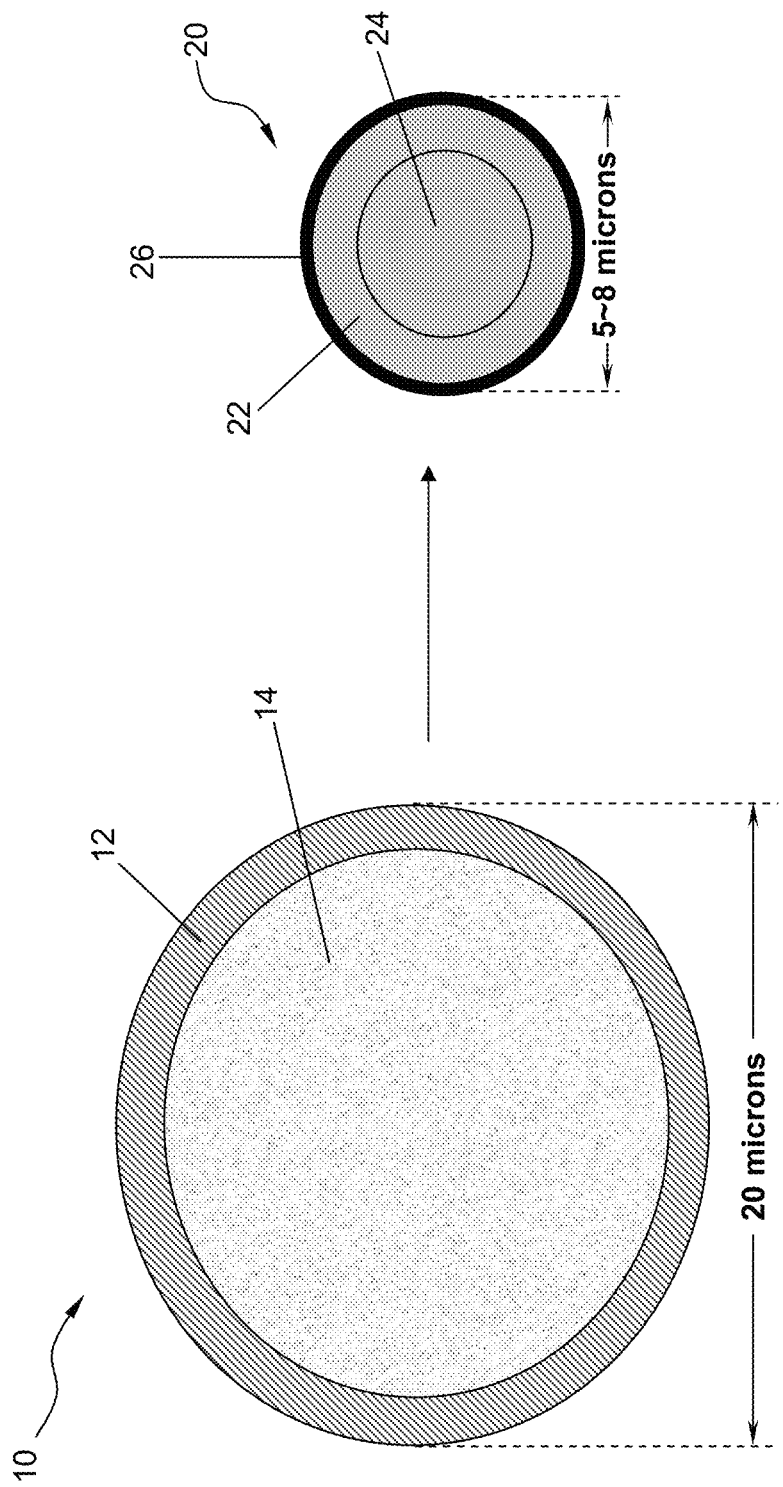
FIG. 1 represents schematic views of: (1) an untreated hollow microsphere with a deformable polymeric shell and an expandable fluid entrapped therein, and (2) a microsphere, containing a collapsed polymeric shell with solid particles entrapped therein and a liquid-impermeable membrane coated thereover, which is formed by processing the untreated hollow microsphere according to one embodiment of the present invention.

The present invention provides stabilized particulate components that are useful in cosmetic or topical compositions, as well as methods for stabilizing particulate components. Specifically, the particulate components are entrapped in polymeric microspheres having an average particle size that is at least 10 times, preferably 20 times, more preferably 50 times, and most preferably 100 times, larger than the average particle size of the particulate components themselves. Each of the microspheres comprises a collapsed polymeric shell having entrapped therein one or more solid particles. Preferably, the physical and/or chemical properties of the entrapped solid particles pertaining to or associated with their desired activities in the cosmetic or topical compositions are not adversely affected, while the significantly larger microspheres provide improved structural and spatial stability.

Entrapment of the solid particles is achieved in the present invention by first providing hollow microspheres with deformable polymeric shells having encapsulated therein an expandable fluid. The deformable polymeric shells are comprised of non-crosslinked or weakly crosslinked polymer chains. The microspheres are mixed with, either sequentially in any order, or simultaneously, a first organic solvent capable of swelling but not dissolving the polymeric shells of the hollow microspheres and solid particles to be entrapped. The gelled mixture thus-formed contains microspheres with polymeric shells in a gelled state, which have been sufficiently swelled so as to have micro-channels or through-holes formed therein to substantially simultaneously allow entry of the solid particles into the microspheres and exit of some of the expandable fluid from the interior of the microspheres, thereby collapsing or imploding of the polymeric shells. While not wishing to be bound by any particular theory, it is believed that the first organic solvent has an ideal combination of properties, including dielectric constant and dipole moment, which impart the solvent with sufficient force to increase the intermolecular distance between the polymer chains of the polymeric shell and implode the microspheres. As the polymeric shells collapse, the polymeric chains realign and entrap the solid particles which are relatively larger than are the expandable fluid and solvent molecules. Nevertheless, the polymer shells still retain some porosity, i.e., that is, some solid particles may still penetrate the polymer shells. Thereafter, a second solvent, miscible with the first solvent, is introduced to the gelled mixture to dilute the first solvent, thereby quenching or de-gelling the mixture. The quenching causes the release of the remainder of the expandable fluid, the solvents, and other volatiles, such as diethanol amine and monomers remaining from the manufacture of the microspheres, resulting in separated microspheres, each having a collapsed polymeric shell, and having one or more solid particles entrapped therein. As a result of the implosion, the microspheres shrink in size from about, for example, 20-150 microns to about 1-50 microns, such as from about 1-15 microns, for example, from about 5-8 microns. The imploded or collapsed microspheres are no longer hollow but are filled with a substantially uniform distribution of solid particles with virtually no empty space remaining in the interior of the microspheres. The mixture is then dried, resulting in a free-flowing powder. Preferably, but not necessarily, a film-forming material is coated over the collapsed polymeric shells to form a liquid-impermeable membrane thereon. The membrane functions to isolate the collapsed polymeric shells of the microspheres from any solvent in the surrounding environment that may swell or otherwise affect the structural integrity of such polymeric shells. In this manner, the solid particles can be even more securely entrapped inside the microspheres with little or no risk of leaking out.

The hollow microspheres as initially provided (i.e., before mixing with the solid particles and the first organic solvent) are preferably expandable hollow polymeric microspheres, each of which contains a deformable polymeric shell that is gas-tight and has enclosed or encapsulated therein an expandable fluid. Upon heating, the enclosed or encapsulated fluid can expand volumetrically to apply pressure on the interior wall of the deformable polymeric shell. At the same time, the elevated temperature may cause the polymeric shell to soften, thereby allowing the entire microsphere to expand in a manner similar to a balloon.

The deformable polymeric shells of the hollow microspheres can be formed of any synthetic or natural crosslinked or un-crosslinked polymer. If the polymer is crosslinked, it is preferred that it is weakly crosslinked. Preferably, but not necessarily, the polymeric shells of the hollow microspheres comprise at least one synthetic polymer obtained by polymerization of one or more ethylenically unsaturated monomers to form homopolymers or copolymers of ethylenically unsaturated monomers or copolymers of ethylenically unsaturated monomers and one or more organic groups. Examples of ethylenically unsaturated monomers that may be suitable include, for example, vinylidene chloride, vinyl chloride, acrylonitrile, acrylic acid and its corresponding $C_1$-$C_{20}$ aliphatic or aromatic esters, methacrylic acid and its corresponding $C_1$-$C_{20}$ aliphatic or aromatic esters, acrylamide, methacrylamide, vinyl pyrrolidone, alkenes such as styrene, ethylene, propylene, butylene, methylpentene, 1,3-butadiene, and the like. The polymeric shells of the hollow microspheres may also be formed of suitable synthetic polymers, such as polyesters, polyamides, polyphthalamides, polyimides, polycarbonates, polyketones, cellulose acetate, polysulfones, polyphenylene sulfides, polyphenylene oxides, polylactic acids, polyvinylpyrrolidone, polystyrene, polyacrylonitrile, polyacrylamide, polymethylmethacrylate, polyacrylates, and copolymers of the above-listed polymers. In a particularly preferred embodiment, the deformable polymeric shells of the hollow microspheres are formed of a copolymer of vinylidene chloride, acrylonitrile, and/or methyl methacrylate.

The expandable fluid inside the hollow microspheres of the present invention may be any suitable gas (e.g., air or nitrogen) or volatile liquid hydrocarbons (e.g., isobutane or isopentane). Preferably, the expandable fluid is selected from the group consisting of air, nitrogen, isobutane, and isopentane. More preferably, the expandable fluid is either isobutane or isopentane.

Hollow microspheres having deformable polymeric shells comprised of a copolymer of vinylidene chloride, acrylonitrile, and methylmethacrylate with an expandable fluid comprised of isobutane or isopentane are commercially available under the trade name of EXPANCEL® from Expancel, Inc. at Duluth, Ga. The EXPANCEL® hollow microspheres are available in various forms, e.g., dry, wet, unexpanded or pre-expanded. Both the dry, unexpanded microspheres (EXPANCEL® DU) and the dry, expanded microspheres (EXPANCEL® DE) can be used in the present invention for entrapping and stabilizing the solid particles. The EXPANCEL® DU microspheres have an average particle size ranging from about 6 to about 40 microns and a density of about 1-1.3 g/cm³. The EXPANCEL® DE microspheres have an average particle size ranging from about 20 to about 150 microns and a density of about 0.03-0.07 g/cm³.

Organic solvents useful in the present invention are those demonstrating adequate thermodynamic "goodness" or sufficient energy to sufficiently swell, but not dissolve, the polymeric shells of the hollow microspheres described hereinabove. Suitable solvents may be aprotic polar, protic polar or non-polar.

Aprotic polar solvents that can be used in practicing the present invention include, but are not limited to, acetone, methyl ethyl ketone, ethyl acetate, tetrahydrofuran, dichloromethane, acetonitrile, dimethylformamide, dimethyl sulfoxide, hexamethylphosphoramide, tetramethylene sulfoxide, N-acetyl piperidine, N-methylpyrrolidinone, N-formylhexamethyleneimine, trimethylene sulfide, N-n-butylpyrrolidinone, diisopropyl sulfoxide, N-formylpiperidine, N-acetylpyrrolidinone, tetrahydrothiophene, N,N-dimethylacetamide, cyclooctanone, cycloheptanone, and di-n-butyl sulfoxide. Acetone, used at room temperature, is preferred. However, other aprotic polar solvents may be used below the temperature at which a 1 wt. % mixture of polymer in solvent becomes homogeneous (i.e., dissolves). As an example, Table 1 lists polar aprotic solvents which may be used, below the indicated temperature, to swell a polymeric shell of poly (vinylidene chloride).

TABLE 1

| Aprotic Solvents | |
|---|---|
| Solvent | Temperature, °C. |
| hexamethylphosphoramide | −7.2 |
| tetramethylene sulfoxide | 28 |
| N-acetylpiperidine | 34 |
| N-methylpyrrolidinone | 42 |
| N-formylhexamethyleneimine | 44 |
| trimethylene sulfide | 74 |
| N-n-butylpyrrolidinone | 75 |
| diisopropyl sulfoxide | 79 |
| N-formylpiperidine | 80 |
| N-acetylpyrrolidinone | 86 |
| tetrahydrothiophene | 87 |
| N,N-dimethylacetamide | 87 |
| cyclooctanone | 90 |
| cycloheptanone | 96 |
| di-n-butyl sulfoxide | 98 |

Suitable protic polar solvents that can be used in practicing the present invention include, but are not limited to, n-butanol, isopropanol, n-propanol, ethanol and methanol. To acquire sufficient energy to increase the intermolecular distance between polymer chains, such solvents may be used at elevated temperatures in a range of from about 55° C. to a temperature below the boiling point of the solvent.

As suitable non-polar solvents, mention may be made of pentane, cyclopentane, hexane, cyclohexane, benzene, toluene, 1,4-dioxane, chloroform, diethylether, 1,3 dibromopropane, bromobenzene, 1-chloronaphthalene, 2-methylnaphthalene and o-dichlorobenzene. Such solvents may be used below the temperature at which a 1 wt. % mixture of polymer in solvent becomes homogeneous (i.e., dissolves). As an example, Table 2 lists non-polar solvents which may be used, below the indicated temperature, to swell a polymeric shell of poly (vinylidene chloride).

TABLE 2

| Solvent | temperature ° C. |
|---|---|
| pentane | 36.1 |
| cyclopentane | 49.3 |
| hexane | 69 |
| cyclohexane | 80.7 |
| benzene | 80.1 |
| toluene | 110.6 |
| 1,4-dioxane | 101.1 |
| chloroform | 61-62 |
| diethyl ether | 34.6 |
| 1,3-dibromopropane | 126 |
| bromobenzene | 129 |
| 1-chloronaphthalene | 134 |
| 2-methylnaphthalene | 134 |
| o-dichlorobenzene | 135 |

Although a preferred embodiment of the present invention in which a microsphere having a polymer shell made of a polyvinylidene chloride has been described, those of skill in the art would be sufficiently guided as to selecting appropriate first solvents useful in carrying out the present invention.

The second solvent useful in the methods according to the present invention are any which are miscible with the first organic solvent. As an example, solvents miscible with acetone include, but are not limited to, acetonitrile, benzene, butanol, carbon tetrachloride, chloroform, cyclohexane, 1,2-dichloroethane, dichlormethane, dimethyl formamide dimethyl sulfoxide, dioxane, ethanol, ethyl acetate, ethyl ether, heptanes, hexane, iso-octane, isopropyl alcohol, methanol, methyl-t-butyl ether, methyl ethyl ketone, pentane, tetrahydrofuran, toluene, water and xylene. In a preferred embodiment of the present invention, where acetone is the first solvent, water is preferred for use as the second solvent. One skilled in the art would readily be guided in selecting the second solvent based on the selection of the first polar solvent.

The solid particles to be entrapped and stabilized according to the present invention can be any particulate components that are commonly used in cosmetic or topical compositions, which include, but are not limited to: mineral pigments and fillers such as, for example, talc, kaolin, mica, bismuth oxychloride, chromium hydroxide, barium sulfate, polymethylmethacrylates (PMMA), boron nitride, nylon beads, polymeric powders (e.g., BPD 500 powders comprised of hexamethylene diisocyanate/trimethylol hexylactone crosspolymer and silica that is commercially available from Kobo Products, Inc. at South Plainfield, N.J.), silica, silica beads, lakes (e.g., aluminum or calcium lake), metal oxides (e.g., black, yellow or blue iron oxide, chromium oxide, zinc oxide, and titanium dioxide), physical and chemical sunscreen agents, and any other organic and inorganic powders or particles. Preferably, but not necessarily, the solid particles are comprised of a material capable of generating free oxygen radicals, and more preferably a metal oxide such as zinc oxide or titanium dioxide. The solid particles can be of any regular or irregular shape, such as, for example, spherical, cubic, cylindrical, planar, fibrous, and the like. The average particle size of the solid particles as used in the present invention should be significantly smaller than that of the hollow microspheres, so that the solid particles can readily enter and be entrapped by the hollow microspheres. Preferably, the average particle size of the solid particles is less than 1 micron, more preferably from about 0.001 micron to about 0.1 micron, and most preferably from about 0.01 to about 0.05 micron. A particular preferred example of the solid particles includes a manganese modified titanium dioxide particle commercially available under the trade name of Optisol™ from Croda, Inc. at Edison, N.J.

As described hereinabove, the hollow microspheres, the first organic solvent and the solid particles are mixed together, either simultaneously or sequentially, to form a gelled mixture. If mixed sequentially, the ingredients can be added and mixed in any suitable order. For example, the hollow microspheres and the solid particles can be blended together first, followed by addition of the first organic solvent to form a slurry. For another example, the solid particles can be dispensed in the first organic solvent, and then mixed with the hollow microspheres. For still another example, the hollow microspheres can be added into the first organic solvent to form a gel, and the solid particles can then be added to the gel. In preferred embodiments of the present invention, the microspheres and the solid particles are mixed together and then added to the first organic solvent, or the microspheres, the solid particles and the first organic solvent are all mixed together simultaneously. In any event, once combined, all the ingredients are well mixed until a homogenous mixture is formed. In order to swell the polymeric shell, the liquid portion of the slurry is substantially pure solvent, that is, from greater than about 95% up to 100% by total weight of the slurry, is required. The slurry may not contain greater than 5%, preferably no greater than 2%, and most preferably, does not contain any, other solvent or other materials, including, but not limited to, oil phase ingredients, for example, waxes, which would dilute the first polar solvent and thus reduce the force needed to swell the polymer shell and thus increase the intermolecular distance between polymer chains. The weight ratio between the hollow microspheres and the first organic solvent is preferably from about 1:3 to about 1:100 and more preferably from about 1:20 to about 1:50, so that the polymeric shells of the hollow microspheres can be sufficiently swelled by the solvent. The weight ratio between the solid particles and the hollow microspheres can range widely from about 1:10 to about 100:1, preferably from about 2:3 to about 10:1, and more preferably from about 1:1 to about 2:1.

Because the polymeric shells of hollow microspheres are comprised of a non-crosslinked or weakly crosslinked polymer, as mentioned hereinabove, the polar organic solvent molecules, which are sufficiently small in comparison with the polymeric molecules, can enter between the polymeric chains, interrupt the intermolecular bonds between neighboring polymeric chains, and pull the polymeric chains apart from each other. Consequently, the polymeric shells of the hollow microspheres are swelled by the first organic solvent, so as to form a gelled mixture that contains porous networks of interconnected polymeric chains spanning or dispersed throughout the volume of the first organic solvent. The polymeric shells of the microspheres in such a gelled state are not longer gas-tight, but have become porous, i.e., with sufficiently large micro-channels therein to allow entry of the solid particles into the sufficiently swelled microspheres. At the same time, the expandable fluid exits from such microspheres through the micro-channels, causing the gelled polymeric shells to collapse or implode and resulting in shrunk microspheres with significantly decreased overall volume. In this manner, the solid particles become entrapped within the collapsed polymeric shells of the shrunk microspheres.

Such shrunk microspheres have an average particle size ranging from about 1 to 50, such as from 1 to 15 microns, for example, from about 5 microns to about 8 microns. The shrunk microspheres are significantly smaller in size than the untreated hollow microspheres. Further, the shrunk microspheres are no longer hollow, but are now filled by the solid particles with little or no empty space left therein. At the same time, the polymeric shells of the microspheres remain in a gelled state, collapsed but somewhat porous. It is important to note that the shrunk microspheres of the present invention, although morphologically and volumetrically modified by the gelling process, remain as separate particles in the gelled mixture with little or no coalescence. Subsequent quenching and drying of the gelled mixture therefore forms fine free-flowing powders, which contain microspheres with well-defined surface boundaries and minimum clumping or agglomeration.

The gelling process as described herein is fundamentally different from the well known sol gel process. In a typical sol-gel process, metal alkoxide and metal chloride precursors are first solubilized to form a solution (sol) and then undergo hydrolysis and polycondensation reactions to form a colloid system composed of solid particles dispersed in a solvent, followed by evolvement toward the formation of an inorganic network containing a liquid phase (gel), which can be dried to remove the liquid phase from the gel thus forming a porous material. In contrast, the gelling process of the present invention does not involve hydrolysis or polycondensation reactions, and it forms a network of water-insoluble polymeric chains dispersed in the first organic solvent.

Due to the miscibility of the first organic solvent and the second solvent, the microspheres become more spatially separated from one another and therefore more dispersed. Such further dispersion of the microspheres functions to minimize the risk of coalescence during subsequent drying of the gelled mixture. Further separation of the microspheres can be achieved by a filtration or centrifugation step, which is optional for the purpose of the present invention.

After the quenching step, both the first organic solvent and the second solvent are preferably removed from the gelled mixture to form dry, free-flowing powders containing the microspheres with the solid particles entrapped therein. Removal of the solvents can be readily achieved by various separation and/or drying techniques well known in the art, such as decantation, centrifugation, filtration, solvent extraction, air drying, vacuum drying, freeze drying, spray drying, fluid bed drying, supercritical fluid drying, and the like. To minimize agglomeration between the dried microspheres, the resulting powders can be further subject to milling and sieving through one or more screens.

In order to eliminate or minimize the potential risk of the entrapped solid particles leaking out of the dried microspheres, the resulting dry, free-flowing powders are coated or otherwise surface-treated with a film-forming material, which forms a liquid-impermeable membrane over each of the dried microspheres. In this manner, the dried microspheres are sealed from solvents in the surrounding environment, which may potentially re-swell the polymeric shells of the microspheres and cause the entrapped solid particles to leak out.

Any material capable of forming a liquid-impermeable membrane, either hydrophilic or hydrophobic, can be used in the present invention. Suitable materials include film-forming materials such as natural or synthetic homo- or co-polymers comprised of ethylenically unsaturated monomers including acrylic acid, methacrylic acid or their $C_1$-$C_{10}$ alkyl esters, ethylene, propylene, or vinylpyrrolidones; silicone gums, which are organosiloxanes generally having a viscosity ranging from about 200,000 to 10,000,000 centipoise at room temperature; animal-derived (e.g., beeswax), plant- or vegetable-derived (e.g., carnauba or candililla waxes), silicone, or mineral (e.g., cerusin) waxes; organic ester or hydrocarbon oils (e.g., paraffin wax), or silicone resins such as trimethylsiloxy silicate or polymethylsilsesquioxane; cellulosic polymers; fatty acids (e.g. fatty carboxylic acids having from about 6 to 40 carbon atoms that may be liquid, solid or semi-solids at room temperature), fatty alcohols (e.g. alcohols having from 6 to 50 carbon atoms that may be liquid, solid, or semi-solid at room temperature), and inorganic materials. Preferably, but not necessarily, the film-forming material comprises an alkyl silicone polymer or more specifically a fatty alkylmethylsiloxane, such as cetyl dimethicone, stearyl dimethicone, or behenyl dimethicone, or other modified siloxanes, such as polyoxyalkylenated silicones typically referred to as dimethicone copolyol or cetyl dimethicone copolyol. For example, a polymethylhydrogensiloxane, which is commercially available from Dow Corning Corporation at Midland, Mich. under the trade name of Dow Corning® MH 1107 fluid, can be used as the film-forming material in the present invention. This polymethylhydrogensiloxane material is a colorless silicone liquid that can be heat cured in the presence of a catalyst (e.g., zinc octoate, iron octoate, dibutyl tin dilaurate, and tin octoate) to form a solid, liquid-impermeable membrane comprised of cross-linked dimethicone over the microspheres of the present invention. For another example, silicone copolymers commercialized by Dow Corning under the trade name of BIO-PSA, which are formed by condensing dimethiconol to MQ resin in the presence of ammonia (the dimethiconol being silanol end-blocked polydimethylsiloxanes, and the MQ resin being a soluble 3-dimensional network comprised of $SiO_{4/2}$ units (Q) and $R^1R^2R^3SiO_{1/2}$ units (M) where $R^1$, $R^2$ and $R^3$ are principally methyl or hydroxyl groups) can also be used as film-forming materials in the present invention to form the liquid-impermeable membrane over the microspheres. Among various types of BIO-PSA materials available from Dow Corning, the Dow Corning® 7-4404, 7-4405, and 7-4411 fluids (containing trimethylated silica treated with dimethylsiloxane and dispersed in a cosmetically acceptable solvent, such as octamethyltrisiloxane, isododecane, or decamethyltetrasiloxane) are particularly preferred.

The resulting microspheres with the solid particles entrapped therein and the liquid-impermeable membrane coated thereover may have an average particle size ranging from about 1 to about 50 microns, more preferably from about 1 to about 15 microns, and most preferably from about 5 to about 8 microns, as determined by a Malvern Particle Size Analyzer, available from Malvern Instrument at Worcestershire, UK. The entrapped solid particles may account for from about 10% to about 90% of the total weight of the resulting microspheres, more preferably 30% to about 75% of the total weight, and most preferably from about 40% to about 60% of the total weight. The polymeric shells may account for from about 5% to about 75% of the total weight of the resulting microspheres, more preferably from about 10% to about 60% of the total weight, and most preferably from about 30% to about 50% of the total weight. The liquid-impermeable coating material may account for from about 1% to about 30% of the total weight of the resulting microspheres, more preferably from about 5% to about 20% of the total weight, and most preferably from about 10% to about 15% of the total weight.

FIG. 1 illustratively shows schematic views of an untreated hollow microsphere 10 and a microsphere 20 according to one embodiment of the present invention, which is formed by processing the untreated hollow microsphere 10 according to the method described hereinabove. Specifically, the untreated hollow microsphere 10 includes a gas-tight and deformable polymeric shell 12 with an expandable fluid 14 entrapped therein. The diameter of the untreated hollow microsphere 10 is approximately 20 microns. In contrast, the microsphere 20 of the present invention includes a collapsed polymeric shell 22 with solid particles 24 entrapped therein and a liquid-impermeable membrane 24 coated thereover. The diameter of the microsphere 20 is significantly smaller than that of the untreated hollow microsphere 10 and approximately ranges from about 5 to about 8 microns.

Figure 2:
FIG. 2 is a Scanning Electron Microscopy (SEM) image of microspheres formed by entrapping $TiO_2$ particles in EXPANCEL® microspheres, according to one embodiment of the present invention.

FIG. 2 shows a Scanning Electron Microscopy (SEM) image of collapsed EXPANCEL® microspheres with TiO₂ particles entrapped therein, which were formed according to the treatment method of the present application as described hereinabove. The SEM picture was taken at 15K× magnification.

When formulated into topical compositions, the microsphere-entrapped solid particles of the present invention provide various advantages and benefits that are not available in their un-encapsulated or "naked" counterparts. For example, because the entrapped solid particles are sealed off from potentially destabilizing or degrading active ingredients in the topical composition, they are significantly more stable than their un-encapsulated or "naked" counterparts. Further, if the solid particles are potentially capable of degrading or otherwise interfering with other active ingredients in the topical composition, the entrapment of such solid particles functions to reduce the interference or degradation and improves the overall stability of the topical composition. Entrapment by microspheres may also alter the hydrophobicity or hydrophilicity of the solid particles and allow such solid particles to be formulated into aqueous, oil or silicone phases that are typically incompatible with un-encapsulated or "naked" solid particles. It is important to note that the desired chemical and/or physical properties of the solid particles should remain substantially unaffected by the entrapment described hereinabove.

Because the microspheres of the present invention are formed by entrapping solid particles in pre-formed, hollow polymeric microspheres that are subsequently collapsed during the entrapment process, rather than conventional in situ formation of polymeric coatings or matrixes around the solid particles, the microspheres of the present invention are characterized by substantially more uniform particle sizes and reduced agglomeration between the microspheres. Further, the entrapment process of the present invention allows the solid particles to be entrapped into microspheres that are many times larger in size than the solid particles themselves (e.g., 10×, 20×, 50×, or 100×) within a relatively short period of time, while the conventional in situ coating or matrix-forming process is very time-consuming and can only form microspheres of limited sizes.

Although applicable to any cosmetic or topical ingredient or component of solid, particulate form, it is believed that the present invention is particularly useful for stabilizing solid particles capable of generating free oxygen radicals without adversely affecting the desired properties of such particles, while at the same time eliminating any potential interaction between such free-oxygen-radical-generating solid particles and other cosmetic or topical ingredients in the formulations that are susceptible to oxidative decomposition or degradation. For example, solid particles formed of certain metal oxides, such as zinc oxide and titanium dioxide, are known to have photoprotective characteristics and can therefore be used as physical sunscreen agents. However, such metal oxide particles in their "naked" or untreated states are known to release free oxygen radicals upon exposure to UV light. Such free oxygen radicals are strong oxidants, which are capable of oxidatively degrading other cosmetic or topical components in the surrounding environments, such as, for example, organic dyes or organic sunscreen agents that are typically susceptible to oxidative decomposition or degradation. Entrapment of such free-oxygen-radical-generating metal oxide particles by the microspheres of the present invention has been shown to effectively eliminate or reduce formation or release of the free oxygen radicals from such particles upon UV exposure, without adversely affecting the sunscreen properties of such metal oxide particles. Consequently, the microsphere-entrapped metal oxide particles of the present invention can be ready used with organic compounds that are known to be susceptible to oxidative decomposition or degradation to form topical or cosmetic compositions with significantly improved overall stability and prolonged shelf life.

The microsphere-entrapped solid particles of the present invention can be added directly to any pharmaceutically or cosmetically acceptable carrier to form a cosmetic or topical composition. For purpose of the present invention, pharmaceutically or cosmetically acceptable carriers are substances that are biologically compatible with human skin and can be used to formulate active ingredients described hereinabove and/or hereinafter into a cream, gel, emulsion, liquid, suspension, powder, nail coating, skin oil, or lotion that can be topically applied. In the case where the cosmetically acceptable carrier is in the form of an emulsion, it may contain from about 0.1 to 99%, preferably from about 0.5 to 95%, more preferably from about 1 to 80% by weight of the total composition of water and from about 0.1 to 99%, preferably from about 0.1 to 80%, more preferably from about 0.5 to 75% by weight of the total composition of oil. In the case where the composition is anhydrous it may comprise from about 0.1 to 90 wt % of oil and from about 0.1 to 75 wt % of other ingredients such as pigments, powders, non-aqueous solvents (such as mono-, di-, or polyhydric alcohols, etc. In the case where the composition is in the form of an aqueous based gel, solution, or suspension, it may comprise from about 0.1 to 99 wt % of water and from about 0.1 to 75 wt % of other ingredients such as botanicals, non-aqueous solvents, etc.

Suitable components of the pharmaceutically or cosmetically acceptable carrier include, but are not limited to: moisturizing agents, astringent agents, chelating agents, sequestrants, emulsifiers/surfactants, emollients, preservatives, stabilizers, abrasives, adsorbents, thickeners, gellants, solidifying/structuring agents, anti-caking agents, anti-foaming agents, pH buffering/adjusting agents, binders, film formers, humectants, pigments, opacifiers, essential oils, fragrances, and aromatic compounds. The pharmaceutically or cosmetically acceptable carrier or carriers can be present in the topical or cosmetic composition of the present invention at an amount ranging from about 1% to about 99.9%, preferably from about 50% to about 99.5%, more preferably from about 70% to about 99%, and most preferably from about 80% to 90% by total weight of the topical or cosmetic composition.

The topical or cosmetic composition may contain one or more skin care additives, which are agents that provide benefits to the skin, rather than merely improving the physical or aesthetic characteristics of the topical composition. If present, such skin care actives may range from about 0.01 to 50%, preferably from about 0.05 to 35% by weight of the total composition. Exemplary skin care additives that can be used in the topical or cosmetic compositions of the present invention include, but are not limited to: sunscreen agents, self-tanning agents, anti-aging agents, anti-wrinkle agents, anti-acne agents (e.g., resorcinol, salicylic acid, and the like), enzyme-inhibiting agents, collagen-stimulating agents, agents for the eradication of age spots and keratoses, analgesics, anesthetics, antimicrobials (e.g., antibacterials, anti-yeast agents, antifungal agents, and antiviral agents), antidandruff agents, antidermatitis agents, antipruritic agents, antiemetics, anti-inflammatory agents, antihyperkeratolytic agents, antiperspirants, antipsoriatic agents, antiseborrheic agents, antihistamine agents, skin lightening agents, depigmenting agents, skin soothing/healing agents (e.g., aloe vera extract, allantoin, and the like), corticosteroids, hormones, antioxidants, proteins or peptides, vitamins and derivatives thereof (e.g., vitamin A, vitamin E, vitamin $B_3$, vitamin $B_5$, and the like), exfoliants, retinoids (e.g., retinoic acid and retinol), farnesol, bisabolol, phytantriol, glycerol, urea, guanidine (e.g., amino guanidine), clotrimazole, ketoconazole, miconozole, griseofulvin, hydroxyzine, diphenhydramine, pramoxine, lidocaine, procaine, mepivacaine, monobenzone, erythromycin, tetracycline, clindamycin, meclocycline, minocycline, hydroquinone, naproxen, ibuprofen, theophylline, cromolyn, albuterol, topical steroids (e.g., hydrocortisone, hydrocortisone 21-acetate, hydrocortisone 17-valerate, and hydrocortisone 17-butyrate), betamethasone valerate, betamethasone diproprionate, benzoyl peroxide, crotamiton, propranolol, promethazine, and mixtures or derivatives thereof. In a preferred, but not necessary embodiment of the present invention, the topical composition comprises one or more skin care actives selected from the group consisting of sunscreen agents, self-tanning agents, anti-aging agents, anti-wrinkle agents, anti-acne agents, antimicrobials, anti-inflammatory agents, skin-lightening agents, antioxidants, proteins or peptides, vitamins and derivatives thereof, exfoliants, and mixtures thereof.

For example, the topical or cosmetic compositions of the present invention may include one or more antioxidants, and more preferably one or more water-soluble extracts of biological materials that exhibit anti-oxidant activities. If present, such antioxidants or water-soluble extracts with anti-oxidant activities may range from about 0.01 to 45%, preferably from about 0.05 to 20%, more preferably from about 0.1 to 15% by weight of the total composition. Examples of suitable water-soluble extracts that exhibit anti-oxidant activities include, but are not limited to, extracts from: artemia, phytosphingosine, polygonum cuspidatum root, yeast such as *saccharomyces* lysate, thermos thermophillus ferment, birch (*Betula alba*), mimosa tenuiflora (bark) extract, fruit, clove, rye, malt, corn, spelt, millet, barley, oat, wheat, sesame, cumin, turmeric, green onion, celery, ginseng, ginger, licorice, carrot, bupleurum root, *Ginkgo biloba* (gingko), Foeniculi Fructus (fennel), kiwi, berry such as *Morus bombycis* (mulberry), *Gentiana lutea* (gentian), algae such as red algae, *Arctium lappa* (burdock), *Salvia officinalis* (sage), *Lentinus edodes* (shiitake mushroom), *Perilla frutescens* (perilla), Filipendula Multijuga, *Fucus vesiculosis* (bladderwrack, sea weed), peach kernel, *Allium sativum* (garlic), *Poria cocos* (poria), *Humulus lupulus* (hops), Mutan Cortex (Moutan Bark), *Pimpinella major, Lactuca sative* (lettuce), *Astragalus membranaceous* (astragalus) and *Rosmarinus officinalis* (rosemary), *Prunus amygdalus* (almond), *Althea officinale* (althea), aloe, Rosae Fructus (rose fruit, or *Rosa multiflora*), *Scuttelaria baicalensis* (Huang qin), Puerariae Radix (Pueraria Root, or *Pueraria lobata*), chamomile such as Chamomillae Flos (German chamomile), *Gardenia jasminoides* (zhii zi, Gardeniae Fructus), *Sophora flavescens* Aiton (Sophorae Radix), chlorella, rice bran, *Paeoniae lactiflora* (white peony), ziyu (*Sanguisorba officinalis*, burnet), *Morus alba* (sang bai pi, mulberry), *Glycine max* (soybean), *Camellia sinensis* (tea), Carthami Flos (safflower), *Aesculus hippocastanum* (horse chestnut), *Melissa officinalis* (lemon balm) and Coicis Semen (*Coix lacryma-jobi* var. *ma-yuen*), *Angelica keisukei*, *Arnica montana* (arnica), *Foeniculum officinale* (fennel), *Isodon japonicus* Hara (Isodonis Herba), Daucus Carota (carrot), *Oryza sativa* (rice), *Crataegus cuneata* (Japanese howthorn), *Acores calamus* (sweet flag), *Crataegus oxycantha* (howthorn), *Juniperus communis, Ligusticum wallichii* (Chinese lovage), Swertiae Herba (Swertia Herb), *Thymus vulgaris* (garden thyme), *Citrus reticulata* (*Citrus unshiu*), *Capsicum tincture, Angelicae sinensis* (angelica), Aurantii Pericarpium (bitter orange peel), *Ruscus aculeatus* (butcher's bloom), *Vitis vinifera* (grape), *Tilia japonica* (lime), *Citrus junos* and *Rosa canina* (rose hip), caffeine, Cinnamomi Cortex (cinnamon bark) and *Eriobotrya japonica* Lindl. (loquat), Gambir, Echinacea, Phellodendri Cortex (amur cork tree or *Phellodendron amurense*), *Hypericum perforatum* (St. John's wort), *Citrus sinensis* (orange), *Valeriana fauriei* Briquet, *Artemisia capillaris* Thunb., *Cucumis sativus* (cucumber), Geranii Herba (Geranium Herb), *Lithospermum erythrorhizon* Sieb. et Zucc., *Hedera helix, Achillea millefolium* (yarrow), *Ziziphus jujuba* (Chinese dates), *Calendula officinalis* (pot marigold), *Houttuynia cordata* (Houttuyniae Herba, Houttuynia Herba), *Potentilla erecta, Petroselinum crispum* (parsley), *Parietaria officinalis, Santalum album* (sandalwood), *Prunus persica* (peach), *Centaurea cyanus* (cornflower), *Eucalyptus globulus* (eucalyptus) and *Lavandula angustifolia* (lavender), *Persea americana* (avocado), *Nasturtium officinalis* (watercress), *Symphytum officinale* (comfrey), *Asarum sieboldii* (wild ginger), *Xanthoxyum piperitum* (Japan pepper), *Rehmannia glutinosa* (di huang), *Mentha piperita* (peppermint), *Syzygium aromaticum* (clove), *Tussilago farfara* (coltsfoot) and *Haematoxylum campechianum* (logwood); Oolong tea, *Cinchona succirubra* (peruvian bark), *Betula verrucosa* (birch) and *Glechoma hederacea* (ground ivy), milk and royal jelly, honey, cysteine and derivatives thereof, ascorbic acid and derivatives thereof, BHA, BHT, ferulic acid and derivatives thereof, grapeseed extract, pine bark extract, horseradish extract, hydroquinones, rosmarinic acid, coffee robusta seed, caffeic acid, tocopherol and derivatives thereof, green tea extract, sodium DNA, sodium ribonucleic acid, octyl, propyl and dodecyl gallates, uric acid and thiodiproprionate derivatives.

In a preferred, but not necessary, embodiment of the present invention, one or more of the antioxidant agents as listed hereinabove are co-entrapped into the microspheres together with the particulate components of the present invention. Such co-entrapment can be achieved, for example, by mixing such antioxidant agents together with the particulate components, the hollow microspheres, and the polar organic solvent during the gelling step to form the gelled mixture. Antioxidant agents particularly preferred for co-entrapment with the particulate components of the present invention include, for example, tetrahydrocurcuminoids, ascorbyl tocopheryl maleate (also referred to as 2-CME), grape seed extract, and rosemary extract. A blend or mixture containing all of these particularly preferred antioxidant agents in equal or substantially equal quantities is most preferred for the practice of the present invention. Such co-entrapped antioxidant agents can most effectively scavenge or abate free oxygen radicals generated by the entrapped metal oxide particles, due to their direct contact therewith or spatial proximity thereto.

The antioxidant agents as listed hereinabove can also be used to form an antioxidant coating over the microspheres, which further scavenges or neutralizes free oxygen radicals released therefrom. Further, the antioxidant agents can be provided in a solubilized or dispersed form in the cosmetically or pharmaceutically acceptable carrier of the topical or cosmetic compositions of the present application. Such solubilized or dispersed antioxidant agents function to scavenge or neutralize free oxygen radicals dispersed in the topical or cosmetic compositions, regardless of the source of such free oxygen radicals, thereby further improving the overall stability of the topical or cosmetic compositions of the present invention.

In a particularly preferred embodiment of the present invention, the topical or cosmetic composition is a sunscreen composition comprising microsphere-entrapped zinc oxide particles, or microsphere-entrapped titanium dioxide particles, or both. As mentioned hereinabove, zinc oxide or titanium dioxide particles are known to have photoprotective characteristics and can therefore be used as physical sunscreen agents, but their uses in topical or cosmetic compositions are limited due to their photo-activity, i.e., their tendency to release free oxygen radicals upon exposure to UV light, which may degrade or otherwise interfere with certain organic cosmetic ingredients or skin care actives that are susceptible to oxidative decomposition or degradation. The entrapment of zinc oxide and/or titanium dioxide particles by the microspheres as described in the present invention effectively eliminates or reduces free oxygen radicals from such particles upon UV exposure, but without adversely affecting the sunscreen properties of such particles.

Consequently, the microsphere-entrapped zinc oxide and/or titanium dioxide particles of the present invention can be ready formulated with organic cosmetic ingredients or skin care additives that are known to be susceptible to oxidative decomposition or degradation to form stable sunscreen compositions with significantly improved overall stability and prolonged shelf live. For example, the microsphere-entrapped zinc oxide and/or titanium dioxide particles of the present invention can be formulated with one or more organic dyes susceptible to oxidative decomposition or degradation to form color cosmetic compositions that also have sunscreen properties. For another example, the microsphere-entrapped zinc oxide and/or titanium dioxide particles of the present invention can be formulated with one or more organic sunscreen agents susceptible to oxidative decomposition or degradation, thereby forming sunscreen compositions that are not only characterized by high SPF values (e.g., SPF 30 or more), but also surprisingly and unexpectedly improved overall stability and prolonged shelf life. If present, such organic sunscreen agents may range from about 0.1 to 45% by weight of the total composition.

Exemplary organic sunscreen agents that can be used in combination with the microsphere-entrapped zinc oxide or titanium dioxide particles of the present invention include, but are not limited to UVA and UVB sunscreens, such as benzophenones and derivatives thereof (e.g., benzophenone-3, dioxybenzone, sulisobenzone, octabenzone, hydroxy- and/or methoxy-substituted benzophenones, and benzophenone-sulfonic acids and salts thereof); salicylic acid derivatives (e.g., ethylene glycol salicylate, triethanolamine salicylate, octyl salicylate, homomethyl salicylate, and phenyl salicylate); urocanic acid and derivatives thereof (e.g., ethyl urocanate); p-aminobenzoic acid (PABA) and derivatives thereof (e.g., ethyl/isobutyl/glyceryl esters thereof and 2-ethylhexyl p-dimethylaminobenzoate, which is also referred to as octyldimethyl PABA); anthranilates and derivatives thereof (e.g., o-amino-benzoates and various esters of amino-benzoic acid); benzalmalonate derivatives; benzimidazole derivatives; imidazolines; bis-benzazolyl derivatives; dibenzoylmethanes and derivatives thereof (e.g., 4-tert-butyl-4'-methoxydibenzoylmethane, which is commonly referred to as "avobenzone," and 4-isopropyl-dibenzoylmethane); benzoazole/benzodiazole/benzotriazoles and derivatives thereof (e.g., 2-(2-hydroxy-5-methylphenyl)benzotriazole and methylene bis-benzotriazolyl tetramethylbutylphenol, which is commonly referred to as "Tinosorb M"); diphenylacrylates and derivatives thereof (e.g., 2-ethylhexyl-2-cyano-3,3-diphenylacrylate, which is commonly referred to as "octocrylene," and ethyl-2-cyano-3,3-diphenylacrylate, which is commonly referred to as "etocrylene"); diesters or polyesters containing diphenylmethylene or 9H-fluorene substitutional groups; 2-phenyl-benzimidazole-5-sulphonic acid (PBSA); 4,4-diarylbutadienes; cinnamates and derivatives thereof (e.g., 2-ethylhexyl-p-methoxycinnamate, octyl-p-methoxycinnamate, umbelliferone, methylumbelliferone, methylaceto-umbelliferone, esculetin, methylesculetin, and daphnetin); camphors and derivatives thereof (e.g., 3-benzylidenecamphor, 4-methylbenzylidenecamphor, polyacrylamidomethyl benzylidenecamphor, benzylidene camphor sulfonic acid, and terephthalylidene dicamphor sulfonic acid, which is commonly referred to as "Encamsule"); triazines and derivatives thereof (e.g., 2,4-bis-{[4-(2-ethyl-hexyloxy)-2-hydroxy]-phenyl}-6-(4-methoxyphenyl)-1,3,5-triazine, which is commonly referred to as "Tinosorb S"); naphthalates and derivatives thereof (e.g., diethylhexyl-2,6-naphthalate); naphtholsulfonates and derivatives thereof (e.g., sodium salts of 2-naphthol-3,6-disulfonic and 2-naphthol-6,8-disulfonic acids); dibenzalacetone and benzalacetonephenone; diphenylbutadienes and derivatives thereof; dihydroxynaphthoic acid and salts thereof; o- and p-hydroxybiphenyldisulfonates; coumarin derivatives (e.g., 7-hydroxy, 7-methyl, and 3-phenyl derivatives thereof); azoles/diazoles/triazoles and derivatives thereof (e.g., 2-acetyl-3-bromoindazole, phenyl benzoxazole, methyl naphthoxazole, and various aryl benzotriazoles); quinine and derivatives thereof (e.g., bisulfate, sulfate, chloride, oleate, and tannate salts thereof); quinoline and derivatives thereof (e.g., 2-phenylquinoline and 8-hydroxyquinoline salts); tannic acid and derivatives thereof (e.g., hexaethylether derivatives thereof); hydroquinone and derivatives thereof; uric acid and derivatives thereof; vilouric acid and derivatives thereof, and mixtures or combinations thereof. Salts and otherwise neutralized forms of certain acidic sunscreens from the list hereinabove are also useful herein. These organic sunscreen agents may be used alone or in combination of two or more. In addition, other known animal or vegetable extracts having UV light-absorbing ability may properly be used alone or in combination.

Organic sunscreen agents that are particularly useful for the practice of the present invention are: 4,4'-t-butyl methoxydibenzoylmethane, 2-ethylhexyl-2-cyano-3,3-diphenylacrylate, 2-ethylhexylsalicylate, 3,3,5-trimethylcyclohexylsalicylate, 2-ethylhexyl p-methoxycinnamate, 2-hydroxy-4-methoxybenzophenone, 2,2-dihydroxy-4-methoxybenzophenone, 2,4-bis-{4-(2-ethyl-hexyloxy)-2-hydroxyl-phenyl}-6-(4-methoxyphenyl)-1,3,5-triazine, methylene bis-benzotriazolyl tetramethylbutylphenol, terephthalylidene dicamphor sulfonic acid, diethylhexyl 2,6-naphthalate, digalloyltrioleate, ethyl 4-[bis(hydroxypropyl)] aminobenzoate, glycerol p-aminobenzoate, methylanthranilate, p-dimethylaminobenzoic acid or aminobenzoate, 2-ethylhexyl p-dimethylaminobenzoate, 2-phenylbenzimidazole-5-sulfonic acid, 2-(p-dimethylaminophenyl)-5-sulfoniobenzoxazoic acid, and mixtures or combinations thereof. Preferably, 4,4'-t-butyl methoxydibenzoylmethane is provided in the sunscreen compositions of the present invention, either with microsphere-entrapped titanium dioxide or microsphere-entrapped zinc oxide, or both. More preferably, the sunscreen compositions of the present invention further include a second organic sunscreen agent selected from the lists provided hereinabove.

The above-described organic sunscreen agents may be solubilized or freely dispersed in the cosmetically or pharmaceutically acceptable carrier of the topical or cosmetic compositions of the present application. Alternatively, the organic sunscreen agents can be provided in a protected form, i.e., encapsulated in protective structures. For example, the organic sunscreen agents can be encapsulated or entrapped into additional microspheres similar to those described hereinabove, i.e., with collapsed polymeric shells. In this manner, the organic sunscreen agents are further protected from free oxygen radicals or other radicals in the surrounding environment that may destabilize or degrade such organic sunscreen agents.

The cosmetically acceptable carrier may also contain one or more oils, which may be silicone, organic, or mixtures thereof. If present, such oils may range from about 0.1 to 99% by weight of the total composition and include volatile or non-volatile silicones such as cyclomethicone; methyl trimethicone; octamethyltrisiloxane; decamethyltetrasiloxane; dodecamethylpentasiloxane; dimethicone; phenyl trimethicone trimethylsiloxyphenyl dimethicone; phenyl dimethicone; cetyl dimethicone; dimethicone copolyol, cetyl dimethicone copolyol; glycerolated silicones such as lauryl PEG-9 polydimethylsiloxyethyl dimethicone; or mixtures thereof. Suitable esters include mono-, di-, or triesters of C4-30 fatty acids and mono-, di-, or polyhydric C1-20 alcohols, such as fatty acid (e.g., stearyl, behenyl, and isostearyl) esters of glycerin, or fatty acid esters of alpha hydroxyl acids such as citric, malic, or lactic acids and the like. Suitable hydrocarbons include monomeric or polymeric olefins or alpha olefins, such as polyisobutene, polydecene, polybutene, or hydrogenated derivatives thereof.

The cosmetically acceptable carrier may also comprise one or more humectants. If present, they may range from about 0.1 to 20% by weight of the total composition and include C1-4 alkylene glycols such as butylene, propylene, ethylene glycol, glycerin and the like.

The cosmetically acceptable carrier may also contain one or more waxes preferably having a melting point ranging from about 30 to 150° C. If present, such waxes may range from about 0.1 to 45% by weight of the total composition and include animal, vegetable, mineral, or silicone waxes. Examples include alkyl dimethicones stearyl dimethicone, candelilla, polyethylene, ozokerite, beeswax, and the like.

The cosmetically acceptable carrier may also comprise one or more organosiloxane elastomers, either emulsifying or non-emulsifying. If present, such elastomers may range from about 0.1 to 30% by weight of the total composition. Examples of suitable elastomers include dimethicone/vinyl dimethicone crosspolymer; dimethicone/dimethicone PEG/ PPG 10/15 crosspolymer; and the like.

The cosmetically acceptable carrier may also include one or more pigments or powders or mixtures thereof. If present, the suggested ranges of such pigments or powders are from about 0.1 to 85% by weight of the total composition. The particle sizes of such pigments or powders may range from about 0.05 to 200 microns but are preferably about 50-100 microns. Examples of pigments include organic pigments such as D&C or FD&C colors or Lakes thereof including blues, browns, reds, etc; or inorganic iron oxides such as brown, yellow, green, red, iron oxides. Suitable powders include titanium dioxide, nylon, PMMA, boron nitride, mica, and the like.

The cosmetically acceptable carrier may also comprise one or more nonionic surfactants, particularly if the topical or cosmetic composition of the present invention is provided in the emulsion form. If present, such surfactants may range from about 0.1 to 20% by weight of the total composition. Suitable surfactants include ethoxylated fatty C6-30 alcohols such as steareth, beheneth, ceteth where the number following each of the surfactants refers to the number of repeating ethylene oxide groups which may range from 2 to 250, e.g. steareth-2, beheth-30 and so on.

The present invention can be further illustrated in the following non-limiting examples.

Example I

A dry mixture was prepared by mixing 60% $TiO_2$ powder and 40% Expancel 551 DE 20d 60 at room temperature, the $TiO_2$ particles adhering to the surface of Expancel microspheres, as monitored by electron microscopy (not shown). The mixture was then poured in industrial grade acetone (3 kg acetone: 1 kg mixture) at room temperature with stirring. As a result, a gelled mixture was formed and the hollow, microspheres of Expancel, having engulfed the particles of $TiO_2$, as monitored by electron microscopy (not shown), collapsed to form spheres having a diameter in the range of from about 6 to 8 microns. The gelling process was then quenched by the addition of water at room temperature (2 volumes water per volume acetone). The resulting slurry was decanted to remove water and acetone, washed three times with water and filtered across 2,000-4,000 mesh via centrifugation at 2,000 rpm with a Heinkel decanter centrifuge. The resulting cake was dried at 75-80° C. in a vacuum under a stream of nitrogen until the cake contained less than 10 ppm acetone as measured by gas chromatography using a Perkin Elmer Clarus 500 Ga Chromatograph. The acetone-free case was ground with a Hammermill 1HP apparatus (Hosokawa Co.) until the total de-aggregation of the cake and the restitution of a powder consisting of particles with a diameter of from about 6 to 8 microns, each powder particle containing $TiO_2$ contributing about 60% of the particle mass. The powder particles were then coated by mixing the particles with an amount of DC7-4404 sufficient to cover the particles with a shell making up about 10% of the overall mass of the powder particle. The wet powder was dried at 74-80° C. in a vacuum under a stream of nitrogen and the resulting cake was milled again to result in a powder consisting of 6 to 8 micron particles.

Example II 800 g Expancel 551 DE 20 d 60 were placed into a mixing chamber. Acetone in an amount of about 6400 g was added under 20 RPM. A gel was formed and about 343 g of ultra fine titanium dioxide ((D(50) 2 microns)) were added to the gel. The combination of titanium dioxide and the gel was mixed until homogeneous. 1500 g of deionized water was added to de-gel the mixture. The acetone and water were removed by heating the combination in a vacuum chamber. The titanium dioxide particles were entrapped in the microspheres and the outer layer of the microsphere was over-coated with about 14 percent by weight of a Dow Corning 1107 silicone polymer. The final particle size of the $TiO_2$-entrapping microspheres, measured using a Malvern Particle Size Analyzer, available from Malvern Instrument Scirocco 2000 at Worcestershire, UK, was between 5 to 8 microns.

Example III

Following the process outlined in Example II, but using Expancel 461 DE 40 d60, the same result was obtained, the final particle size of the TiO$_2$-entrapping microspheres being measured as between 5 to 8 microns.

Example IV

Example II was repeated with irregular solid particles of Dow Chemical Saran F 310 (Polyvinylidene Chloride). This experiment was performed in order to prove ability of particles to be dispersed in a gelled polymer, regardless of their original shape or composition.

Example V 300 g Expancel 551 DE 20 d 60 were placed into a mixing chamber. Acetone in an amount of about 4000 g was added under 20 RPM. A gel was formed and about 463 g of ultra fine zinc dioxide ((D(50) 2 microns)) were added to the gel. The combination of zinc dioxide and the gel was mixed until homogeneous. Then 10,000 g of deionized water was added. The acetone and water were removed by heating the combination in a vacuum chamber. The zinc oxide particles were entrapped in the microspheres and the outer layer of the microsphere was over-coated with about 10 percent by weight of a Dow Corning 7-4404 cosmetic fluid. The final particle size of the ZnO-entrapping microspheres, measured using a Malvern Particle Size Analyzer, available from Malvern Instrument at Worcestershire, UK, was between 5 to 8 microns.

Example VI

A comparative test was conducted to show photodegradation of an organic dye, namely, D&C Red No. 28 (or Red 28), under UV exposure and in the presence of various TiO$_2$ particles, either un-encapsulated (i.e., naked) or entrapped with or without antioxidants in microspheres of the present invention as described hereinabove.

Specifically, an ethanol solution containing 0.013 wt % of Red 28 was provided as a control sample. Several comparative samples were then prepared, which respectively contained: (1) 0.011 wt % of Red 28 and 0.02 wt % of un-encapsulated or naked TiO$_2$ particles with an average particle size of about 20-50 nm as dispersed in ethanol; (2) 0.011 wt % of Red 28 and 0.04 wt % of TiO$_2$-entrapping microspheres with co-entrapped antioxidants (which contain titanium dioxide, aluminum hydroxide/stearic acid, polyvinylidene chloride/acrylonitrile copolymer, methicone, and tetrahydrocurcuminoids) as dispersed in ethanol; and (3) 0.011 wt % of Red 28 and 0.04 wt % of TiO$_2$-entrapping microspheres without any antioxidants (which contain titanium dioxide, aluminum hydroxide/stearic acid, polyvinylidene chloride/acrylonitrile copolymer, and methicone) as dispersed in ethanol.

Light transmission at a wavelength of about 400-700 nm by the control sample and the comparative samples before any UV exposure were measured by a Spectroflash SF600 Plus-CT colorimeter commercially available from DataColor at Lawrenceville, N.J. The control sample and the comparative samples were then exposed to UV light of about 275 J. After the UV exposure, light transmission at 400-700 nm by the control sample and comparative samples were measured again and compared with the light transmission values before the UV exposure, and DE color shifts of about 7.34 for the control sample, 9.32 for the TiO$_2$-entrapping microspheres without any antioxidants, 3.89 for the TiO$_2$-entrapping microspheres with co-entrapped antioxidants, and 82.77 for un-encapsulated or naked TiO$_2$ particles were calculated based on such measurements.

Figure 3:
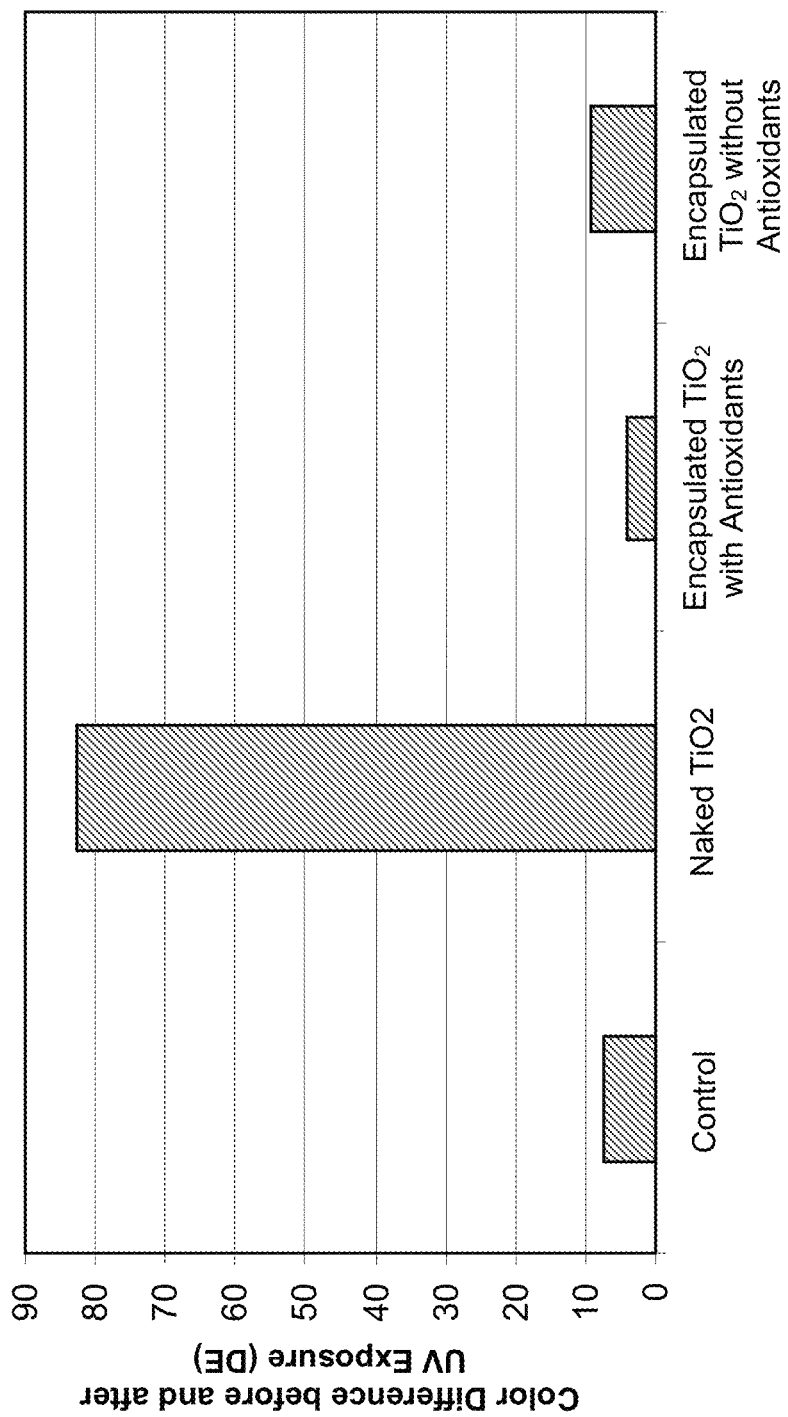
FIG. 3 is a graph showing percentage color changes (%) of an organic dye (Red 28) after 22 hours of exposure to ultraviolet (UV) light, while the organic dye was provided either alone as a control sample or in combination with various types of $TiO_2$ particles, including un-encapsulated (or naked) $TiO_2$ particles and microsphere-entrapped $TiO_2$ particles either with or without antioxidants, according to alternative embodiments of the present invention.

FIG. 3 is a graph showing the percentage color changes of various samples described hereinabove, which include (from left to right): the control sample, the comparative sample (1), the comparative sample (2) and the comparative sample (3). It is clear from FIG. 3 that when combined with un-encapsulated or naked TiO$_2$ particles, a majority of the organic dye Red 28 was degraded upon UV exposure, while entrapment of the TiO$_2$ particles into the microspheres of the present invention, either with or without antioxidants, effectively reduced the degradation of such organic dye to a level that was either comparable with or lower than the control sample.

Example VII

A comparative test was conducted to show UV absorbance spectra of un-encapsulated (or naked) TiO$_2$ particles and microsphere-entrapped TiO$_2$ particles of the present invention.

The following two formulas (I and II), one of which contained naked TiO$_2$ particles and the other of which contained microsphere-entrapped TiO$_2$ particles of the present invention, were prepared:

| Components | wt % in Formula I (with Naked TiO$_2$) | wt % in Formula II (with Entrapped TiO$_2$) |
| --- | --- | --- |
| Deionized water | 35.07 | 30.59 |
| Naked TiO$_2$ (titanium dioxide/aluminum hydroxide/stearic acid in trioctyldodecyl citrate) | 17.40 | — |
| Microsphere-entrapped TiO$_2$ (titanium dioxide, aluminum hydroxide/stearic acid, polyvinylidene chloride/acrylonitrile copolymer, and methicone) | — | 13.00 |
| Butylene glycol | 8.00 | 8.00 |
| Cyclopentasiloxane | 7.00 | 6.00 |
| Isopropyl titanium triisostearate/C$_{12}$-C$_{15}$ alkyl benzoate/polyglyceryl-6 polyricinoleate/zinc oxide/caprylyl methicone | 6.00 | 6.00 |
| Tricaprylin | 3.42 | 3.00 |
| Trioctyldodecyl citrate | 2.75 | 11.52 |
| Steareth-2 | 2.42 | 2.42 |
| Tricaprylyl citrate | 2.00 | 2.50 |
| Silica | 2.00 | 2.00 |
| Dipentaerythrityl tri-polyhydroxystearate | 2.00 | 2.00 |
| Stearyl dimethicone | 1.93 | 1.93 |
| Lecithin | 1.00 | 1.00 |
| Calcium sulfate | 1.00 | 1.00 |
| Titanium dioxide/methicone | 1.00 | 1.00 |
| Barium sulfate | 1.00 | 1.00 |
| Sorbitan tristearate | 0.77 | 0.77 |
| Magnesium aluminum silicate | 0.60 | 0.60 |
| Silver borosilicate | 0.50 | 0.50 |
| Dimethicone | 0.50 | 0.50 |
| PEG-40 stearate | 0.41 | 0.41 |
| Ceteth-2 | 0.41 | 0.41 |
| PEG/PPG-18/18 dimethicone | 0.40 | 1.50 |
| Xanthan gum | 0.40 | 0.40 |
| Iron oxide yellow | 0.40 | 0.33 |
| Phosphoric acid | 0.30 | 0.30 |
| Tocopheryl acetate (Vitamin E) | 0.25 | 0.25 |
| Magnesium ascorbyl phosphate | 0.25 | 0.25 |
| Steareth-20 | 0.22 | 0.22 |
| Disodium EDTA | 0.20 | 0.20 |
| Pantethine | 0.10 | 0.10 |
| Sodium stearate | 0.10 | 0.10 |
| BHT | 0.10 | 0.10 |
| Bisabolol | 0.05 | 0.05 |
| Iron oxide red | 0.02 | 0.02 |
| Iron oxide black | 0.02 | 0.02 |

Figure 4:
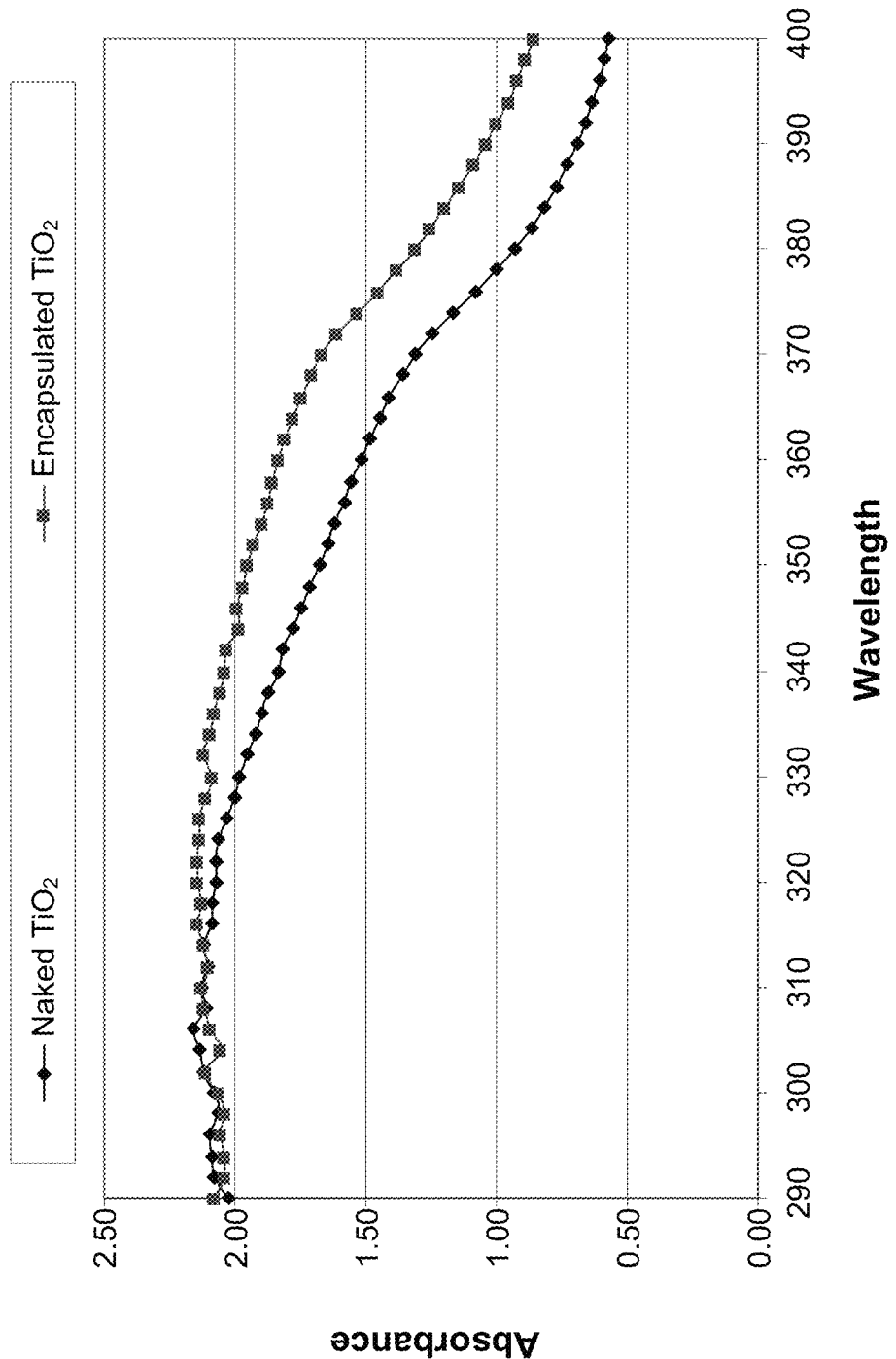
FIG. 4 shows UV absorption spectra of sunscreen compositions containing either un-encapsulated (or naked) $TiO_2$ particles or microsphere-entrapped $TiO_2$ particles of the present invention after exposure to UV light.

The above-described two formulas were exposed to UV light of about 225 J emitted by a Thermo Oriel-Solar simulator manufactured by Newport Corporation at Stanford, Conn. The photo-absorbance of the two formulas during the UV exposure was measured by a Radiometer/Photometer manufactured by International Light Technologies at Peabody, Mass. and plotted in FIG. 4. It is clear from FIG. 4 that in comparison with un-encapsulated or naked $TiO_2$ particles, the microsphere-entrapped $TiO_2$ particles demonstrated comparable absorbance at the UVB range (at wavelength about 280-315 nm) and significantly higher absorbance at the UVA range (at wavelength about 315 nm-400 nm).

Example VIII

A comparative test was conducted to show photostability of 4,4'-t-butyl methoxydibenzoylmethane (Avobenzone) in the presence of un-encapsulated or naked $TiO_2$ particles and the microsphere-entrapped $TiO_2$ particles of the present invention.

The following two formulas (III and IV), one of which contained naked $TiO_2$ particles and the other of which contained microsphere-entrapped $TiO_2$ particles of the present invention, were prepared:

| Components | wt % in Formula III (with Naked $TiO_2$) | wt % in Formula IV (with Entrapped $TiO_2$) |
|---|---|---|
| Deionized water | 51.50 | 44.90 |
| Coated $TiO_2$ (titanium dioxide/aluminum hydroxide/stearic acid in trioctyldodecyl citrate) | 17.40 | — |
| Microsphere-entrapped $TiO_2$ (polyvinylidene chloride/acrylonitrile copolymer, titanium dioxide, stearic acid, aluminum hydroxide, and methicone) | — | 13.00 |
| Neopentyl glycol diheptanoate | 9.50 | 9.50 |
| Butylene glycol | 4.00 | 4.00 |
| Cetearyl olivate/sorbitan olivate | 4.00 | 4.00 |
| Kukui nut oil | 3.00 | 3.00 |
| Avobenzone | 3.00 | 3.00 |
| Lauryl PEG-9 polydimethylsiloxyethyl dimethicone | 3.00 | 3.00 |
| Hydrogenated olive oil/olive oil/olive oil unsaponifiables | 2.00 | 2.00 |
| Dimethicone | 1.00 | 1.00 |
| Cetyl alcohol | 0.75 | 0.75 |
| Silver borosilicate | 0.50 | 0.50 |
| Xanthan gum | 0.25 | 0.25 |
| Disodium EDTA | 0.10 | 0.10 |
| Trioctyldodecyl citrate | — | 11.00 |

Figure 5A:
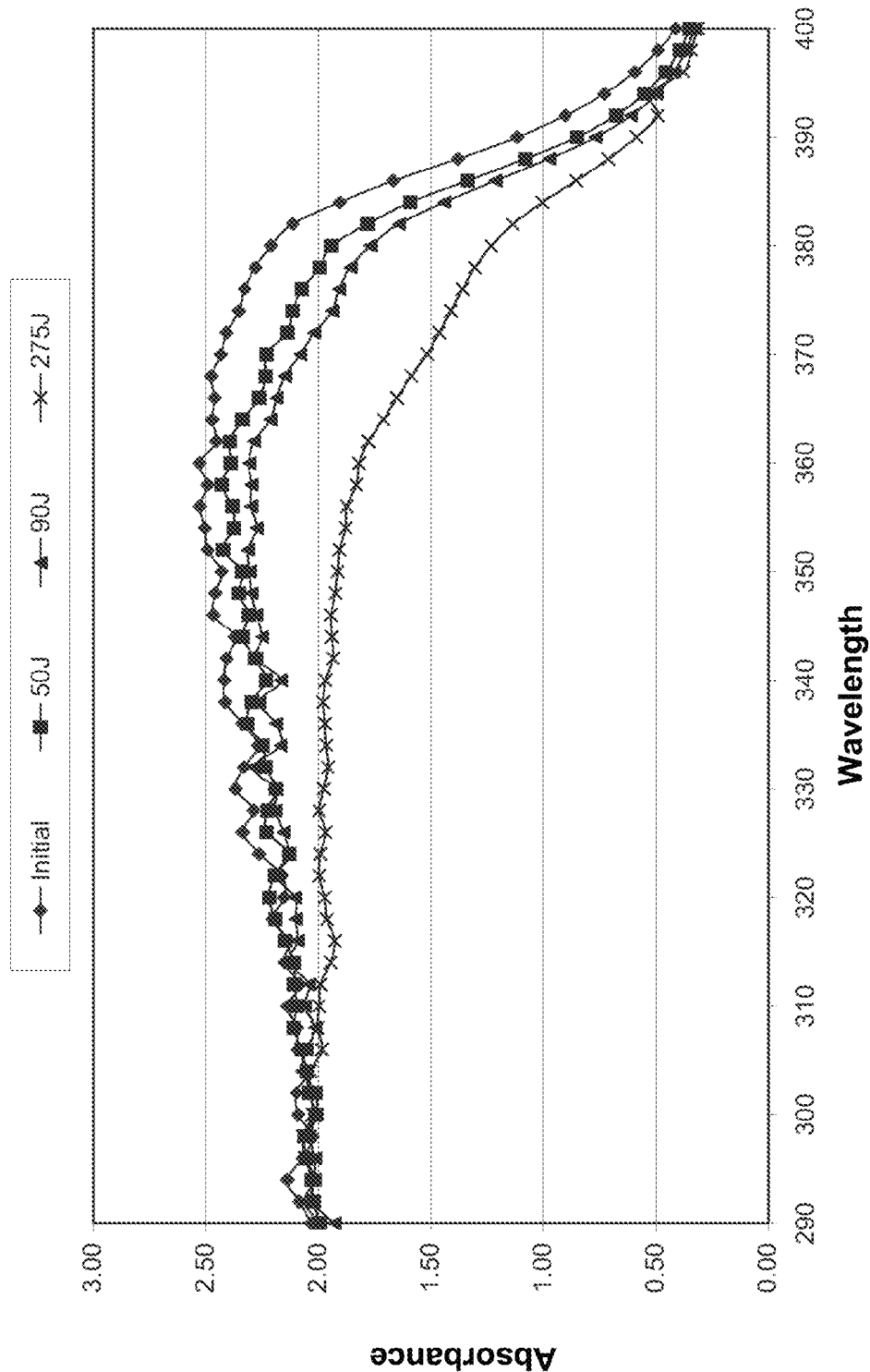
FIG. 5A shows photo-absorbance curves of a sunscreen composition containing un-encapsulated (or naked) $TiO_2$ particles and avobenzone, after exposure to UV light at various intensities.
Figure 5B:
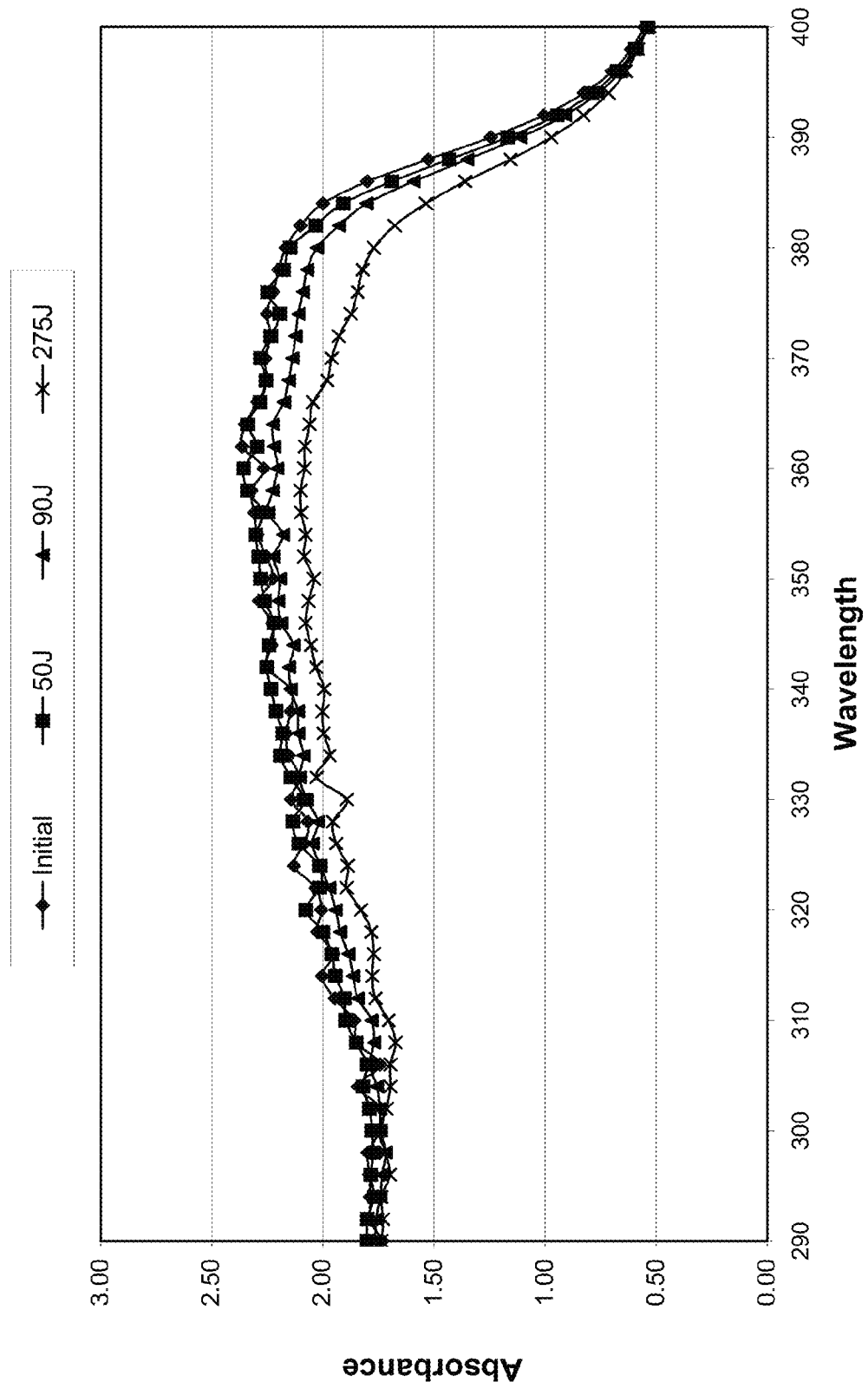
FIG. 5B shows photo-absorbance curves of a sunscreen composition containing microsphere-entrapped $TiO_2$ particles of the present invention and avobenzone, after exposure to UV light at various intensities.

The above-described two formulas were exposed to UV light at various intensities, namely, 50 J, 90 J, and 275 J, emitted by a Thermo Oriel-Solar simulator manufactured by Newport Corporation at Stratford, Conn. The photo-absorbance of these two formulas before and after the UV exposure was measured by a Radiometer/Photometer manufactured by International Light Technologies at Peabody, Mass. 01960. The initial photo-absorbance of such formulas before the UV exposure was recorded as the baseline values. FIG. 5A shows the photo-absorbance curves of Formula III at the initial state (i.e., before the UV exposure) and after exposure to UV light at 50 J, 90 J, and 275 J. FIG. 5B shows the photo-absorbance curves of Formula IV at the initial state (i.e., before the UV exposure) and after exposure to UV light at 50 J, 90 J, and 275 J.

It is clear that when combined with naked $TiO_2$ particles, avobenzone was significantly less photo-stable than when combined with the microsphere-entrapped $TiO_2$ particles of the present invention, which is demonstrated by the significantly greater reduction in the photo-absorbance of Formal III in comparison with that of Formula IV after exposure to UV light at a higher intensity (e.g., 275 J), as shown in FIGS. 5A and 5B.

Example IX

Following are several exemplary topical or cosmetic sunscreen formulas containing either microsphere-entrapped $TiO_2$ particles or microsphere-entrapped ZnO particles of the present invention.

Sunscreen Formula 1

This face lotion is an oil-in-water emulsion containing the microsphere-entrapped $TiO_2$ particles of the present invention (without any co-entrapped antioxidant) in combination with several organic sunscreen agents including Avobenzone:

| Components | wt % |
|---|---|
| Deionized water | 35.08 |
| Disodium EDTA | 0.10 |
| Sodium dehydroacetate | 0.10 |
| Acetyl glucosamine | 0.05 |
| Caffeine | 0.20 |
| Butylene glycol | 2.00 |
| Dehydroxanthan gum | 0.25 |
| Avobenzone | 3.00 |
| Ethylhexyl salicylate | 5.00 |
| Benzophenone-3 | 5.00 |
| Polyester-8 | 3.00 |
| Butyloctyl salicylate | 4.00 |
| $C_{30}$-$C_{38}$ olefin/isopropyl maleate/MA copolymer | 0.75 |
| VP/eicosene copolymer | 0.75 |
| Potassium cetyl phosphate | 1.00 |
| PEG-100 stearate | 2.25 |
| Glyceryl stearate | 1.50 |
| Cetyl alcohol | 0.75 |
| Stearic acid | 0.75 |
| Homosalate | 5.00 |
| Kukui nut oil | 3.00 |
| Dipentaerythrityl tri-polyhydroxystearate | 1.50 |
| Turmeric root extract | 0.01 |
| Microsphere-entrapped $TiO_2$ (titanium dioxide, aluminum hydroxide/stearic acid, polyvinylidene chloride/acrylonitrile copolymer, and methicone) | 6.00 |
| Mica | 5.00 |
| Lauryl PEG-9 polydimethylsiloxyethyl dimethicone | 2.00 |
| Methyl trimethicone | 5.00 |
| Caprylyl methicone | 1.50 |
| Ethylhexyl glycerin | 0.50 |
| Phenoxyethanol/caprylyl glycol/sorbic acid | 0.85 |
| Ammonium acryloyldimethyltaurate/VP copolymer | 0.20 |
| Mulberry root extract/*scutellaria baicalensis* extract/grape extract | 0.10 |
| Yeast extract | 0.01 |
| Whey protein | 0.01 |
| Fragrance | 0.20 |

Sunscreen Formula 2

This face lotion is an oil-in-water emulsion containing the microsphere-entrapped ZnO particles of the present invention (without any co-entrapped antioxidant) in combination with several organic sunscreen agents including Avobenzone:

| Components | wt % |
|---|---|
| Deionized water | 30.86 |
| Disodium EDTA | 0.10 |
| Dipentaerythrityl tri-polyhydroxystearate | 2.00 |
| Butylene glycol | 4.00 |
| Xanthan gum | 0.20 |

-continued

| Components | wt % |
|---|---|
| Acrylic acid/VP crosspolymer | 0.25 |
| Avobenzone | 3.00 |
| Ethylhexyl salicylate | 5.00 |
| Mica | 5.00 |
| Polyester-8 | 3.00 |
| Butyloctyl salicylate | 3.50 |
| Neopentyl glycol diheptanoate | 2.50 |
| $C_{30}$-$C_{38}$ olefin/isopropyl maleate/MA copolymer | 0.80 |
| Octocrylene | 2.79 |
| Cetyl alcohol | 0.75 |
| VP/eicosene copolymer | 0.50 |
| Potassium cetyl phosphate | 1.00 |
| PEG-100 stearate | 2.25 |
| Glyceryl stearate | 1.50 |
| Homosalate | 5.00 |
| Kukui nut oil | 6.00 |
| Benzophenone-3 | 5.00 |
| Styrene/acrylates copolymer//PEG-8 laurate//water | 1.00 |
| Microsphere-entrapped ZnO (zinc oxide, isopropyl titanium, triisostearate, polyvinylidene chloride/acrylonitrile copolymer, and methicone) | 6.00 |
| Lauryl PEG-9 polydimethylsiloxyethyl dimethicone | 2.00 |
| Methyl trimethicone | 3.00 |
| Caprylyl methicone | 1.50 |
| Ethylhexyl glycerin | 0.50 |
| Phenoxyethanol/caprylyl glycol/sorbic acid | 0.85 |
| Trometamine | 0.15 |

Sunscreen Formula 3

This face lotion is a water-in-silicone emulsion containing the microsphere-entrapped $TiO_2$ particles of the present invention (without any co-entrapped antioxidant):

| Components | wt % |
|---|---|
| Deionized water | 41.68 |
| Dipentaerythrityl tri-polyhydroxystearate | 2.00 |
| Butylene glycol | 6.00 |
| Xanthan gum | 0.25 |
| Glycerin | 2.00 |
| Phenoxyethanol/caprylyl glycol | 0.85 |
| Phenoxyethanol | 0.20 |
| Magnesium sulfate | 1.00 |
| Cetyl PEG/PPG-10/1 dimethicone | 1.00 |
| Titanium dioxide/methicone | 4.35 |
| Microsphere-entrapped $TiO_2$ (titanium dioxide, polyvinylidene chloride/acrylonitrile copolymer/trimethylated silica) | 8.70 |
| Dimethicone//dimethicone PEG-10/15 crosspolymer | 2.00 |
| Lauryl PEG-9 polydimethylsiloxyethyl dimethicone | 1.00 |
| Dimethicone/vinyl dimethicone crosspolymer//methyl trimethicone | 1.50 |
| Pantethine | 0.50 |
| Tocopheryl acetate | 0.20 |
| Neopentyl glycol diethylhexanoate | 7.50 |
| Polydiethylsiloxane | 3.00 |
| Methyl trimethicone | 16.27 |

Sunscreen Formula 4

This face lotion is an oil-in-water emulsion containing the microsphere-entrapped $TiO_2$ particles of the present invention with co-entrapped antioxidants and in combination with Avobenzone:

| Components | wt % |
|---|---|
| Deionized water | 39.15 |
| Disodium EDTA | 0.10 |
| Caffeine | 0.20 |
| Butylene glycol | 3.00 |
| Dehydroxanthan gum | 0.30 |
| VP/eicosene copolymer | 0.75 |
| Potassium cetyl phosphate | 1.00 |
| PEG-100 stearate | 2.25 |
| Glyceryl stearate | 1.50 |
| Cetyl alcohol | 0.75 |
| Stearic acid | 0.75 |
| Kukui nut oil | 6.00 |
| Dipentaerythrityl tri-polyhydroxystearate | 1.50 |
| Butyloctyl salicylate | 4.00 |
| Neopentyl glycol diheptanoate | 7.00 |
| $C_{30}$-$C_{38}$ olefin/isopropyl maleate/MA copolymer | 0.75 |
| Dioctyl succinate | 10.00 |
| Avobenzone | 3.00 |
| Polyester-8 | 3.00 |
| Microsphere-entrapped $TiO_2$ with antioxidants (titanium dioxide, polyvinylidene chloride/acrylonitrile copolymer/trimethylated silica, and tetrahydrocurcuminoids) | 6.00 |
| Lauryl PEG-9 polydimethylsiloxyethyl dimethicone | 3.00 |
| Methyl trimethicone | 5.00 |
| Ethylhexyl glycerin | 0.30 |
| Phenoxyethanol/caprylyl glycol | 0.50 |
| Ammonium acrylodimethyltaurate/VP copolymer | 0.20 |

Sunscreen Formula 5

This face lotion is an oil-in-water emulsion containing the microsphere-entrapped $TiO_2$ particles of the present invention (without any co-entrapped antioxidant) in combination with several organic sunscreen agents (without Avobenzone):

| Components | wt % |
|---|---|
| Deionized water | 38.08 |
| Disodium EDTA | 0.10 |
| Sodium dehydroacetate | 0.10 |
| Acetyl glucosamine | 0.05 |
| Caffeine | 0.20 |
| Butylene glycol | 2.00 |
| Dehydroxanthan gum | 0.25 |
| Ethylhexyl salicylate | 5.00 |
| Benzophenone-3 | 5.00 |
| Polyester-8 | 3.00 |
| Butyloctyl salicylate | 4.00 |
| Neopentyl glycol diheptanoate | 3.50 |
| $C_{30}$-$C_{38}$ olefin/isopropyl maleate/MA copolymer | 0.75 |
| VP/eicosene copolymer | 0.75 |
| Potassium cetyl phosphate | 1.00 |
| PEG-100 stearate | 2.25 |
| Glyceryl stearate | 1.50 |
| Cetyl alcohol | 0.75 |
| Stearic acid | 0.75 |
| Homosalate | 5.00 |
| Kukui nut oil | 3.00 |
| Dipentaerythrityl tri-polyhydroxystearate | 1.50 |
| Turmeric root extract | 0.01 |
| Microsphere-entrapped $TiO_2$ (titanium dioxide/aluminum hydroxide/stearic acid, polyvinylidene chloride/acrylonitrile copolymer, and methicone) | 6.00 |
| Mica | 5.00 |
| Lauryl PEG-9 polydimethylsiloxyethyl dimethicone | 2.00 |
| Methyl trimethicone | 5.00 |
| Caprylyl methicone | 1.50 |
| Ethylhexyl glycerin | 0.50 |
| Phenoxyethanol/caprylyl glycol/sorbic acid | 0.85 |
| Ammonium acrylodimethyltaurate/VP copolymer | 0.20 |
| Mulberry root extract/*scutellaria baicalensis* extract/grape extract | 0.10 |
| Yeast extract | 0.01 |
| Whey protein | 0.01 |
| Fragrance | 0.20 |

Sunscreen Formula 6

This face lotion is an oil-in-water emulsion containing the microsphere-entrapped ZnO particles of the present invention (without any co-entrapped antioxidant) in combination with several organic sunscreen agents including Avobenzone:

| Components | wt % |
| --- | --- |
| Deionized water | 33.82 |
| Disodium EDTA | 0.10 |
| Dipentaerythrityl tri-polyhydroxystearate | 2.00 |
| Caprylyl glycol | 0.30 |
| Butylene glycol | 4.00 |
| Xanthan gum | 0.30 |
| Avobenzone | 3.00 |
| Ethylhexyl salicylate | 5.00 |
| Mica | 5.00 |
| Octocrylene | 2.79 |
| Butyloctyl salicylate | 5.00 |
| Neopentyl glycol diheptanoate | 1.50 |
| $C_{30}$-$C_{38}$ olefin/isopropyl maleate/MA copolymer | 0.80 |
| VP/eicosene copolymer | 0.50 |
| Potassium cetyl phosphate | 1.00 |
| PEG-100 stearate | 2.25 |
| Glyceryl stearate | 1.50 |
| Cetyl alcohol | 0.75 |
| Homosalate | 5.00 |
| Kukui nut oil | 5.00 |
| Silica | 2.00 |
| Styrene/acrylates copolymer//PEG-8 laurate//water | 1.00 |
| Lauryl PEG-9 polydimethylsiloxyethyl dimethicone | 2.00 |
| Methyl trimethicone | 5.00 |
| Dimethicone | 1.50 |
| Microsphere-entrapped ZnO (zinc oxide/diphenyl capryl methicone, polyvinylidene chloride/acrylonitrile copolymer/trimethylated silica) | 7.44 |
| Ethylhexyl glycerin | 0.50 |
| Phenoxyethanol/caprylyl glycol | 0.85 |
| Caprylic/capric triglyceride/*laminaria ochroleuca* extract | 0.10 |

Sunscreen Formula 7

This face lotion is a water-in-silicone emulsion containing the microsphere-entrapped TiO$_2$ particles of the present invention (without any co-entrapped antioxidant):

| Components | wt % |
| --- | --- |
| Deionized water | 39.67 |
| Dipentaerythrityl tri-polyhydroxystearate | 2.00 |
| Butylene glycol | 6.00 |
| Xanthan gum | 0.25 |
| Glycerin | 2.00 |
| Phenoxyethanol/caprylyl glycol | 0.85 |
| Phenoxyethanol | 0.20 |
| Magnesium sulfate | 1.00 |
| Cetyl PEG/PPG-10/1 dimethicone | 1.00 |
| Microsphere-entrapped TiO$_2$ (titanium dioxide/polyvinylidene chloride/acrylonitrile copolymer/trimethylated silica) | 17.40 |
| Dimethicone//dimethicone PEG-10/15 crosspolymer | 2.00 |
| Lauryl PEG-9 polydimethylsiloxyethyl dimethicone | 1.00 |
| Dimethicone/vinyl dimethicone crosspolymer//methyl trimethicone | 1.50 |
| Pantethine | 0.50 |
| Tocopheryl acetate | 0.20 |
| Neopentyl glycol diethylhexanoate | 7.50 |
| Polydiethylsiloxane | 3.00 |
| Methyl trimethicone | 13.92 |
| Sorbitan sesquioleate | 0.01 |

Sunscreen Formula 8

This anhydrous formula, which contains the microsphere-entrapped zinc oxide of the present invention in combination with several organic sunscreen agents including Avobenzone, can be used to form a stick-form bronzer product.

| Components | wt % |
| --- | --- |
| Dipentaerythrityl hexahydroxystearate/stearate/rosinate | 1.50 |
| Bis-diglyceryl polyacyladipate-2 | 13.00 |
| Shea butter | 4.00 |
| Polyglyceryl-2 triisostearate | 6.00 |
| Butyloctyl salicylate | 4.00 |
| Dipentaerythrityl tetrabehenate/polyhydroxystearate//behenic acid//hydroxystearic acid | 5.00 |
| Microcrystalline wax | 5.00 |
| Avobenzone | 3.00 |
| Ethylhexyl salicylate | 5.00 |
| Homosalate | 5.00 |
| Polyester-8 | 3.00 |
| Tridecyl trimellitate | 5.00 |
| Polyethylene | 2.50 |
| Isononyl isononanoate | 1.00 |
| Diethylhexyl carbonate | 8.00 |
| Neopentyl glycol diheptanoate | 3.79 |
| Tricaprylin | 2.75 |
| Mica/iron oxides/titanium dioxide | 1.50 |
| Mica/iron oxides | 0.75 |
| Microsphere-entrapped ZnO (zinc oxide/diphenyl capryl methicone, polyvinylidene chloride/acrylonitrile copolymer/trimethylated silica) | 2.00 |
| Pentaerythrityl tetra-di-t-butyl hydroxyhydrocinnamte | 0.01 |
| Tocopheryl acetate | 0.10 |
| Simethicone | 0.10 |

Sunscreen Formula 9

This anhydrous formula, which contains the microsphere-entrapped zinc oxide of the present invention in combination with several organic sunscreen agents including Avobenzone, can be used to form a gel-type bronzer product.

| Components | wt % |
| --- | --- |
| Hydrogenated polyisobutene | 13.00 |
| Simethicone | 0.10 |
| VP/Eicosene copolymer | 7.00 |
| Dextrin palmitate | 11.00 |
| Hydrogenated polyisobutene | 22.50 |
| Dimethicone | 9.00 |
| Pentaerythrityl tetra-di-t-butyl hydroxyhydrocinnamte | 0.05 |
| Hydrogenated polyisobutene/ethylene/propylene/styrene copolymer/butylene/ethylene/styrene copolymer | 4.50 |
| Dipentaerythrityl hexahydroxystearate/hexastearate/hexarosinate | 1.08 |
| PPG-3 myristyl ether | 1.00 |
| Jojoba butter | 1.00 |
| Butyloctyl salicylate | 4.00 |
| Avobenzone | 3.00 |
| $C_{30}$-$C_{38}$ olefin/isopropyl maleate/MA copolymer | 1.00 |
| Tocopheryl acetate | 0.50 |
| Sweet almond oil | 1.00 |
| Calcium sodium borosilicate/iron oxides | 0.50 |
| Calcium sodium borosilicate/titanium dioxide/iron oxides | 1.50 |
| Mica/iron oxides | 1.50 |
| Ethylhexyl salicylate | 5.00 |
| Homosalate | 5.00 |
| Polyester-8 | 3.00 |
| Jojoba esters | 1.77 |
| Microsphere-entrapped ZnO (zinc oxide/diphenyl capryl methicone, polyvinylidene chloride/acrylonitrile copolymer/trimethylated silica) | 2.00 |

While the present invention has been described hereinabove with reference to specific embodiments, features and aspects, it will be recognized that the invention is not thus limited, but rather extends in utility to other modifications, variations, applications, and embodiments, and accordingly all such other modifications, variations, applications, and embodiments are to be regarded as being within the spirit and scope of the present invention.

What we claim is:
1. A method for modifying or treating solid particles, comprising:
   (a) forming a gelled mixture by mixing either simultaneously or sequentially in any order (1) hollow microspheres each comprising a deformable polymeric shell having entrapped therein an expandable fluid, (2) a first organic solvent which is present in an amount sufficient to swell and implode the microspheres but not dissolve the polymeric shells of the hollow microspheres, and (3) solid particles, wherein molecules of the first solvent enter between polymeric chains of the polymeric shell and disrupt intermolecular bonds between the chains, forming micro-channels in the swelled polymer shells which substantially simultaneously allow entry of the solid particles into the hollow microspheres and exit of a first portion of the expandable fluid therefrom, thereby collapsing the microspheres and entrapping the solid particles therein;
   (b) introducing a second solvent which is miscible with the first solvent into the gelled mixture with sufficient agitation to quench the gelled mixture, thereby diluting the first solvent and permitting exit of a second portion of expandable fluid from the microspheres so as to form separated microspheres, each comprising a collapsed polymeric shell, having an average particle size in the range of from about 1 to about 50 microns, and having one or more of said solid particles entrapped therein; and
   (c) removing the expandable fluid and solvents to result in a dry, free-flowing powder.
2. The method of claim 1, wherein the expandable fluid is selected from the group consisting of gases, air, nitrogen, volatile liquid hydrocarbons, isobutane, and isopentane.
3. The method of claim 1, further comprising:
   (d) coating the microspheres with a film-forming material to form a liquid-impermeable membrane thereon.
4. The method of claim 3, wherein the liquid-impermeable membrane comprises one or more materials selected from the group consisting of acrylate homo- or co-polymers, methacrylate homo- or co-polymers, vinylpyrrolidone homo- or co-polymers, silicone gums, silicone waxes, silicone oils, silicone resins, organic waxes, esters, hydrocarbons, celluloses, fatty acids, fatty alcohols, and inorganic materials.
5. The method of claim 4, wherein the liquid-impermeable membrane comprises crosslinked dimethicone or trimethylated silica treated with dimethyl siloxane.
6. The method of claim 1, wherein the solid particles have an average particle size ranging from about 0.001 micron to about 0.1 micron.
7. The method of claim 1, wherein the collapsed polymeric shell comprises at least one synthetic polymer obtained by polymerization of one or more ethylenically unsaturated monomers selected from the group consisting of vinylidene chloride, vinyl chloride, acrylonitrile, acrylic acid and its $C_1$-$C_{20}$ aliphatic or aromatic esters, methacrylic acid and its $C_1$-$C_{20}$ aliphatic or aromatic esters, acrylamide, methacrylamide, vinyl pyrrolidone, alkenes, styrene, ethylene, propylene, butylene, methylpentene, and 1,3-butadiene.
8. The method of claim 1, wherein the collapsed polymeric shell comprises at least one synthetic thermoplastic polymer selected from the group consisting of polyesters, polyamides, polyphthalamides, polyimides, polycarbonates, polyketones, cellulose acetate, polysulfones, polyphenylene sulfides, polyphenylene oxides, polylactic acids, polyvinylpyrrolidone, polystyrene, polyacrylonitrile, polyacrylamide, polymethylmethacrylate, polyacrylates, and copolymers thereof.
9. The method of claim 1, wherein the collapsed polymeric shell comprises a copolymer of vinylidene chloride, acrylonitrile, and/or methyl methacrylate.
10. The method composition of claim 1, wherein the entrapped solid particles comprise one or more materials selected from the group consisting of talc, kaolin, mica, bismuth oxychloride, chromium hydroxide, barium sulfate, polymethylmethacrylates (PMMA), boron nitride, nylon beads, polymeric powders, silica, silica beads, lakes, metal oxides, iron oxide, chromium oxide, zinc oxide, titanium dioxide, and physical and chemical sunscreen agents.
11. The method of claim 1, wherein the entrapped solid particles comprise one or more materials capable of scavenging free oxygen radicals.
12. The method of claim 1, wherein the entrapped solid particles comprise one or more metal oxides.
13. The method of claim 12, wherein the entrapped solid particles comprise titanium dioxide, zinc oxide, or a combination thereof.
14. The method of claim 1, wherein the average particle size of the microspheres, having a collapsed polymeric shell, is in the range of from about 1-15 microns.
15. The method of claim 14, wherein the average particle size of the microspheres, having a collapsed polymeric shell, is in the range of from about 5-8 microns.
16. The method of claim 1, wherein the first solvent is a polar aprotic organic solvent selected from the group consisting of acetone, methyl ethyl ketone, ethyl acetate, tetrahydrofuran, dichloromethane, acetonitrile, dimethylformamide, dimethyl sulfoxide, hexamethylphosphoramide, tetramethylene sulfoxide, N-acetyl piperidine, N-methylpyrrolidinone, N-formylhexamethyleneimine, trimethylene sulfide, N-n-butylpyrrolidinone, diisopropyl sulfoxide, N-formylpiperidine, N-acetylpyrrolidinone, tetrahydrothiophene, N,N-dimethylacetamide, cyclooctanone, cycloheptanone, and di-n-butyl sulfoxide.
17. The method of claim 1, wherein the first solvent is a polar protic organic solvent selected from the group consisting of n-butanol, isopropanol, n-propanol, ethanol and methanol.
18. The method of claim 1, wherein the first solvent is a non-polar organic solvent selected from the group consisting of pentane, cyclopentane, hexane, cyclohexane, benzene, toluene, 1,4-dioxane, chloroform, diethylether, 1,3 dibromopropane, bromobenzene, 1-chloronapthalene, 2-methylnaphthalene and o-dichlorobenzene.
19. The method of claim 1, wherein the first solvent is acetone and the second solvent is selected from the group consisting of acetonitrile, benzene, butanol, carbon tetrachloride, chloroform, cyclohexane, 1,2-dichloroethane, dichlormethane, dimethyl formamide dimethyl sulfoxide, dioxane, ethanol, ethyl acetate, ethyl ether, heptanes, hexane, iso-octane, isopropyl alcohol, methanol, methyl-t-butyl ether, methyl ethyl ketone, pentane, tetrahydrofuran, toluene, water and xylene.
20. The method of claim 19, wherein the second solvent is water.
21. The method of claim 11, which further comprises at least one organic compound susceptible to oxidative decomposition or degradation.
22. The method of claim 21, wherein said organic compound is an organic sunscreen agent susceptible to oxidative decomposition or degradation.
23. The method of claim 21, wherein said organic compound is an organic dye susceptible to oxidative decomposition or degradation.

24. The method of claim 22, wherein the at least one organic sunscreen agent is selected from the group consisting of 4,4'-t-butyl methoxydibenzoylmethane, 2-ethylhexyl-2-cyano-3,3-diphenylacrylate, 2-ethylhexylsalicylate, 3,3,5-trimethylcyclohexylsalicylate, 2-ethylhexyl p-methoxycinnamate, 2-hydroxy-4-methoxybenzophenone, 2,2-dihydroxy-4-methoxybenzophenone, 2,4-bis-{4-(2-ethylhexyloxy)-2-hydroxyl-phenyl}-6-(4-methoxyphenyl)-1,3,5-triazine, methylene bis-benzotriazolyl tetramethylbutylphenol, terephthalylidene dicamphor sulfonic acid, diethylhexyl 2,6-naphthalate, digalloyltrioleate, ethyl 4-[bis(hydroxypropyl)]aminobenzoate, n-hexyl 2-(4-diethylamino-2-hydroxybenzoyl)benzoate, glycerol p-aminobenzoate, methylanthranilate, p-dimethylaminobenzoic acid or aminobenzoate, 2-ethylhexyl p-dimethylaminobenzoate, 2-phenylbenzimidazole-5-sulfonic acid, 2-(p-dimethylaminophenyl)-5-sulfoniobenzoxazoic acid, and mixtures or combinations thereof.

25. The method of claim 24, wherein the at least one organic sunscreen agent is 4,4'-t-butyl methoxydibenzoylmethane.

26. The method of claim 22, further comprising a second organic sunscreen agent.

27. The method of claim 22, wherein the at least one organic sunscreen agent is encapsulated in protective structures.

28. The method of claim 27, wherein the protective structures comprise additional microspheres with collapsed polymeric shells, into which the at least one organic sunscreen agent is entrapped.

29. The method of claim 1, wherein at least some of the microspheres have titanium dioxide particles entrapped therein.

30. The method of claim 1, wherein at least some of the microspheres have zinc oxide particles entrapped therein.

31. The method of claim 1, wherein some of the microspheres have titanium dioxide particles entrapped therein, and others have zinc oxide particles entrapped therein.

32. The method of claim 1, wherein said one or more antioxidants are co-entrapped with the solid particles inside the collapsed polymeric shell of each microsphere, or coated over the microspheres, or solubilized or dispersed in the cosmetically or pharmaceutically acceptable carrier.

33. A microsphere having a collapsed polymeric shell formed by the method of claim 1.

34. A microsphere having a collapsed polymeric shell formed by the method of claim 3.

35. A topical composition comprising a dispersion of microspheres having collapsed polymeric shells formed by the method of claim 1, in a cosmetically or pharmaceutically acceptable carrier.

36. A topical composition comprising a dispersion of microspheres having collapsed polymeric shells formed by the method of claim 3, in a cosmetically or pharmaceutically acceptable carrier.

37. A topical sunscreen composition comprising a dispersion of microspheres having collapsed polymeric shells formed by the method of claim 3, in a cosmetically or pharmaceutically acceptable carrier, each of said microspheres having entrapped therein one or more solid particles that comprise titanium dioxide, zinc oxide, or a combination thereof, and at least one organic sunscreen agent susceptible to oxidative decomposition or degradation.

\* \* \* \* \*